US012702801B2

(12) United States Patent
Spataro et al.

(10) Patent No.: US 12,702,801 B2
(45) Date of Patent: Aug. 11, 2026

(54) VALVE MODULES AND METHODS FOR INTRODUCER ASSEMBLIES AND RAPIDLY INSERTABLE CENTRAL-CATHETER INSERTION ASSEMBLIES

(71) Applicant: Bard Access Systems, Inc., Salt Lake City, UT (US)

(72) Inventors: Joe Spataro, Cottonwood Heights, UT (US); Kyle G. Thornley, Farmington, UT (US); Eric W. Lindekugel, Salt Lake City, UT (US); Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 424 days.

(21) Appl. No.: 18/367,390

(22) Filed: Sep. 12, 2023

(65) Prior Publication Data

US 2024/0082549 A1 Mar. 14, 2024

Related U.S. Application Data

(60) Provisional application No. 63/405,784, filed on Sep. 12, 2022.

(51) Int. Cl.
*A61M 25/09* (2006.01)
*A61M 1/00* (2006.01)
(Continued)

(52) U.S. Cl.
CPC .............. *A61M 25/09* (2013.01); *A61M 1/74* (2021.05); *A61M 1/81* (2021.05); *A61M 1/84* (2021.05);
(Continued)

(58) Field of Classification Search
CPC .............. A61M 25/09; A61M 25/0021; A61M 25/0043; A61M 25/01; A61M 25/0606;
(Continued)

(56) References Cited

U.S. PATENT DOCUMENTS 3,076,457 A 2/1963 Copen
3,359,978 A 12/1967 Smith, Jr.
(Continued)

FOREIGN PATENT DOCUMENTS

CN 106422031 B 7/2021
CN 114870208 A 8/2022
(Continued)

OTHER PUBLICATIONS

Adam et al. (Gastrointestinal Endoscopy vol. 77, No. 5S 2013, 1020) (Year: 2010).
(Continued)

*Primary Examiner* — Tasnim Mehjabin Ahmed
(74) *Attorney, Agent, or Firm* — Rutan & Tucker LLP

(57) ABSTRACT

Rapidly insertable central-catheter ("RICC") insertion assemblies and associated methods include valve modules. For example, a RICC insertion assembly can include a RICC, an introducer needle, and an access guidewire coupled together by a coupler in which a valve module is disposed. The introducer needle includes a needle shaft having a longitudinal needle slot and a sheath over the needle shaft sealing the needle slot thereunder except for that under a sheath opening of the sheath. The valve module includes an elastomeric gasket encircling at least a portion of a valve-module compartment of the coupler housing. In a ready-to-deploy state of the RICC insertion assembly, the gasket is compressed in the valve-module compartment around both the introducer needle and the access guidewire where the access guidewire extends from the sheath open-
(Continued)

ing, thereby creating a substantially air-tight space within the gasket around the introducer needle and the access guidewire.

22 Claims, 19 Drawing Sheets

(51) Int. Cl.
*A61M 25/00* (2006.01)
*A61M 25/01* (2006.01)
*A61M 25/06* (2006.01)
*A61M 39/06* (2006.01)
*A61M 39/22* (2006.01)

(52) U.S. Cl.
CPC .... *A61M 25/0021* (2013.01); *A61M 25/0043* (2013.01); *A61M 25/01* (2013.01); *A61M 25/0606* (2013.01); *A61M 39/06* (2013.01); *A61M 39/0606* (2013.01); *A61M 39/0613* (2013.01); *A61M 39/22* (2013.01); *A61M 2039/062* (2013.01)

(58) Field of Classification Search
CPC ............ A61M 1/74; A61M 1/81; A61M 1/84; A61M 39/06; A61M 39/0606; A61M 39/0613; A61M 39/22; A61M 2039/062
See application file for complete search history.

(56) References Cited

U.S. PATENT DOCUMENTS 3,539,034 A 11/1970 Tafeen
4,411,654 A 10/1983 Boarini et al.
4,743,265 A 5/1988 Whitehouse et al.
4,886,507 A 12/1989 Patton et al.
4,935,008 A 6/1990 Lewis, Jr.
4,957,489 A 9/1990 Cameron et al.
4,988,356 A 1/1991 Crittenden et al.
4,994,040 A 2/1991 Cameron et al.
5,255,690 A 10/1993 Keith et al.
5,261,887 A 11/1993 Walker
5,290,244 A 3/1994 Moonka
5,380,290 A 1/1995 Makower et al.
5,687,727 A 11/1997 Kraus et al.
5,735,813 A 4/1998 Lewis
5,836,306 A 11/1998 Duane et al.
5,853,391 A 12/1998 Bell
5,971,957 A 10/1999 Luther et al.
6,019,736 A 2/2000 Avellanet et al.
6,159,195 A 12/2000 Ha et al.
7,172,587 B2 2/2007 Poole et al.
7,938,820 B2 5/2011 Webster et al.
8,882,713 B1 11/2014 Call et al.
11,819,638 B2 * 11/2023 Howell .............. A61M 25/0111
11,918,767 B2 * 3/2024 Howell .............. A61M 25/0111
12,161,820 B2 * 12/2024 Howell ............. A61M 25/0668
2002/0004635 A1 1/2002 Yock
2002/0072712 A1 6/2002 Nool et al.
2003/0205843 A1 11/2003 Adams
2004/0092879 A1 5/2004 Kraus et al.
2004/0236346 A1 11/2004 Parker
2005/0021124 A1 1/2005 Cunniffe et al.
2005/0043684 A1 2/2005 Basta et al.
2005/0251092 A1 11/2005 Howell et al.
2006/0129091 A1 6/2006 Bonnette et al.
2007/0100294 A1 5/2007 Sugita et al.
2007/0276288 A1 11/2007 Khaw
2008/0009793 A1 1/2008 Dabbs
2008/0027380 A1 1/2008 Wholey et al.
2008/0091137 A1 4/2008 Reavill
2008/0262430 A1 10/2008 Anderson et al.
2009/0187147 A1 7/2009 Kurth et al.
2011/0071502 A1 3/2011 Asai
2013/0184659 A1 7/2013 Byrnes et al.
2014/0100552 A1 4/2014 Gallacher et al.
2015/0119806 A1 4/2015 Blanchard et al.
2015/0224287 A1 8/2015 Bian et al.
2015/0314109 A1 11/2015 Minar et al.
2015/0320968 A1 11/2015 Konstantino et al.
2016/0175563 A1 6/2016 Woehr et al.
2016/0220786 A1 8/2016 Mitchell et al.
2016/0310704 A1 10/2016 Ng et al.
2017/0035996 A1 2/2017 O'Fallon
2017/0258489 A1 9/2017 Galili et al.
2017/0296792 A1 10/2017 Ornelas Vargas et al.
2018/0043138 A1 2/2018 Chu
2019/0015637 A1 1/2019 Jacobs
2019/0022353 A1 1/2019 Khanicheh et al.
2019/0022359 A1 1/2019 Khanicheh et al.
2019/0038113 A1 2/2019 Chu
2019/0134374 A1 5/2019 Korkuch et al.
2020/0008838 A1 1/2020 Frey et al.
2020/0107859 A1 4/2020 Zhu
2020/0147349 A1 * 5/2020 Holt .................. A61M 25/0606
2020/0170559 A1 6/2020 Burkholz et al.
2020/0188650 A1 6/2020 Al-Ali
2020/0197682 A1 6/2020 Franklin et al.
2021/0085927 A1 * 3/2021 Howell ................ A61M 25/06
2021/0121661 A1 4/2021 Howell
2021/0330941 A1 10/2021 Howell et al.
2021/0332274 A1 10/2021 Hoshi et al.
2021/0361915 A1 11/2021 Howell et al.
2021/0402153 A1 12/2021 Howell et al.
2022/0168548 A1 6/2022 Dong
2022/0362524 A1 11/2022 Howell
2022/0370762 A1 11/2022 Blanchard et al.
2023/0039733 A1 2/2023 Howell
2023/0041261 A1 2/2023 Howell
2023/0043989 A1 2/2023 Howell
2023/0064542 A1 3/2023 Howell
2023/0086639 A1 3/2023 Howell
2023/0096377 A1 3/2023 West et al.
2023/0149667 A1 5/2023 Lindekugel et al.
2023/0181878 A1 6/2023 Blanchard et al.
2023/0201537 A1 6/2023 Howell et al.
2023/0201538 A1 6/2023 Howell et al.
2023/0218867 A1 7/2023 Howell et al.
2023/0381481 A1 11/2023 Pizzato
2024/0226507 A1 7/2024 Spataro
2025/0375594 A1 12/2025 Lindekugel
2026/0021276 A1 1/2026 Blanchard et al.

FOREIGN PATENT DOCUMENTS

DE 4136051 A1 7/1993
DE 19750090 A1 6/1999
EP 0067260 A1 12/1982
EP 0155331 A1 9/1985
EP 0499147 A2 8/1992
EP 0641571 A1 3/1995
EP 1338299 A1 8/2003
EP 3193813 A1 7/2017
EP 3473291 A1 4/2019
JP H02255156 A 10/1990
JP H077971 Y2 3/1995
JP 2004254879 A 9/2004
JP 2009232917 A 10/2009
JP 5101359 B2 12/2012
WO 8906986 A1 8/1989
WO 9509662 A1 4/1995
WO 9810821 A1 3/1998
WO 9959651 A2 11/1999
WO 02078776 A2 10/2002
WO 2005096778 A2 10/2005
WO 2009094089 A1 7/2009
WO 2011143621 A1 11/2011
WO 2012101089 A1 8/2012
WO 2013064215 A1 5/2013
WO 2015061172 A1 4/2015
WO 2016042544 A1 3/2016
WO 2016123278 A1 8/2016
WO 2016187063 A1 11/2016

(56) References Cited

FOREIGN PATENT DOCUMENTS

| | | | |
|---|---|---|---|
| WO | 2020206280 | A2 | 10/2020 |
| WO | 2021216902 | A1 | 10/2021 |
| WO | 2021222116 | A2 | 11/2021 |
| WO | 2022204049 | A1 | 9/2022 |
| WO | 2022246271 | A2 | 11/2022 |
| WO | 2022245774 | A3 | 12/2022 |
| WO | 2023014994 | A1 | 2/2023 |
| WO | 2023018669 | A1 | 2/2023 |
| WO | 2023018729 | A1 | 2/2023 |
| WO | 2023018733 | A1 | 2/2023 |
| WO | 2023028138 | A2 | 3/2023 |
| WO | 2023049174 | A1 | 3/2023 |
| WO | 2023091586 | A1 | 5/2023 |
| WO | 2023114324 | A1 | 6/2023 |
| WO | 2023122312 | A1 | 6/2023 |
| WO | 2023129457 | A1 | 7/2023 |
| WO | 2023137077 | A1 | 7/2023 |
| WO | 2024059073 | A1 | 3/2024 |
| WO | 2024151869 | A1 | 7/2024 |
| WO | 2025259604 | A1 | 12/2025 |

OTHER PUBLICATIONS

Lapalu et al. "Totally implantable port management: impact of positive pressure during needle withdrawal on catheter tip occlusion (an experimental study)" The Journal of Vascular Access 2010; 11: 46-51, 2010 Wichtig Editore, Original Article, 2010.
PCT/US2024/011269 filed Jan. 11, 2024 International Search Report and Written Opinion dated May 15, 2024.
PCT/US2025/032881 filed Jun. 9, 2025 International Search Report and Written Opinion dated Sep. 24, 2025.
U.S. Appl. No. 17/700,152, filed Mar. 21, 2022 Non-Final Office Action dated Aug. 14, 2025.
U.S. Appl. No. 17/750,097, filed May 20, 2022 Notice of Allowance dated Jun. 27, 2025.
U.S. Appl. No. 17/883,490, filed Aug. 8, 2022 Non-Final Office Action dated Jul. 31, 2025.
U.S. Appl. No. 17/884,402, filed Aug. 9, 2022 Notice of Allowance dated Sep. 10, 2025.
U.S. Appl. No. 17/894,759, filed Aug. 24, 2022 Final Office Action dated Sep. 24, 2025.
U.S. Appl. No. 17/949,734, filed Sep. 21, 2022 Non-Final Office Action dated Aug. 4, 2025.
U.S. Appl. No. 17/989,325, filed Nov. 17, 2022 Restriction Requirement dated Aug. 28, 2025.
U.S. Appl. No. 18/081,491, filed Dec. 14, 2022 Non-Final Office Action dated Aug. 22, 2025.
U.S. Appl. No. 18/087,676, filed Dec. 22, 2022 Restriction Requirement dated Oct. 8, 2025.
U.S. Appl. No. 17/700,152, filed Mar. 21, 2022 Restriction Requirement dated Apr. 29, 2025.
U.S. Appl. No. 17/746,113, filed May 17, 2022 Non-Final Office Action dated Apr. 7, 2025.
U.S. Appl. No. 17/884,307, filed Aug. 9, 2022 Non-Final Office Action dated Apr. 2, 2025.
U.S. Appl. No. 17/884,402, filed Aug. 9, 2022 Non-Final Office Action dated May 30, 2025.
U.S. Appl. No. 17/894,759, filed Aug. 24, 2022 Non-Final Office Action dated Jun. 16, 2025.
PCT/US2023/032545 filed Sep. 12, 2023 International Search Report and Written Opinion dated Feb. 13, 2024.
U.S. Appl. No. 17/700,152, filed Mar. 21, 2022 Restriction Requirement dated Jan. 31, 2025.
U.S. Appl. No. 17/746,113, filed May 17, 2022 Restriction Requirement dated Dec. 11, 2024.
U.S. Appl. No. 17/750,097, filed May 20, 2022 Restriction Requirement dated Mar. 20, 2025.
PCT/US2022/039742 filed Aug. 8, 2022 International Preliminary Report on Patentability dated Feb. 13, 2024.
PCT/US2022/041368 filed Aug. 24, 2022 International Preliminary Report on Patentability dated Feb. 27, 2024.
PCT/US2022/044242 filed Sep. 21, 2022 International Preliminary Report on Patentability dated Mar. 26, 2024.
PCT/US2022/053887 filed Dec. 22, 2022 International Search Report and Written Opinion dated May 8, 2023.
U.S. Appl. No. 17/883,490, filed Aug. 8, 2022 Final Office Action dated Dec. 22, 2025.
U.S. Appl. No. 17/884,307, filed Aug. 9, 2022 Final Office Action dated Oct. 23, 2025.
U.S. Appl. No. 17/894,759, filed Aug. 24, 2022 Notice of Allowance dated Dec. 16, 2025.
U.S. Appl. No. 18/081,491, filed Dec. 14, 2022 Final Office Action dated Jan. 12, 2026.
U.S. Appl. No. 18/086,517, filed Dec. 21, 2022 Non-Final Office Action dated Oct. 31, 2025.
U.S. Appl. No. 18/095,968, filed Jan. 11, 2023 Restriction Requirement dated Nov. 24, 2025.
PCT/US2022/021187 filed Mar. 21, 2022 International Search Report and Written Opinion dated Jun. 17, 2022.
PCT/US2022/029561 filed May 17, 2022 International Search Report and Written Opinion dated Nov. 9, 2022.
PCT/US2022/030365 filed May 20, 2022 International Search Report and Written Opinion dated Apr. 4, 2023.
PCT/US2022/039742 filed Aug. 8, 2022 International Search Report and Written Opinion dated Dec. 21, 2022.
PCT/US2022/039852 filed Aug. 9, 2022 International Search Report and Written Opinion dated Dec. 6, 2022.
PCT/US2022/039861 filed Aug. 9, 2022, International Search Report and Written Opinion dated Jan. 5, 2023.
PCT/US2022/041368 filed Aug. 24, 2022 International Search Report and Written Opinion dated Mar. 21, 2023.
PCT/US2022/044242 filed Sep. 21, 2022 International Search Report and Written Opinion dated Feb. 8, 2023.
PCT/US2022/050280 filed Nov. 17, 2022 International Search Report and Written Opinion dated Apr. 17, 2023.
PCT/US2022/052884 filed Dec. 14, 2022 International Search Report and Written Opinion dated May 15, 2023.
PCT/US2022/053724 filed Dec. 21, 2022 International Search Report and Written Opinion dated May 10, 2023.
PCT/US2023/010623 filed Jan. 11, 2023, International Search Report and Written Opinion dated Jul. 6, 2023.
U.S. Appl. No. 17/700,152, filed Mar. 21, 2022 Final Office Action dated Feb. 12, 2026.
U.S. Appl. No. 17/883,490, filed Aug. 8, 2022 Advisory Action dated Mar. 26, 2026.
U.S. Appl. No. 17/949,734, filed Sep. 21, 2022 Final Office Action dated Feb. 5, 2026.
U.S. Appl. No. 17/989,325, filed Nov. 17, 2022 Notice of Allowance dated Jan. 22, 2026.
U.S. Appl. No. 18/086,517, filed Dec. 21, 2022 Final Office Action dated Apr. 7, 2026.
U.S. Appl. No. 18/087,676, filed Dec. 22, 2022 Non-Final Office Action dated Mar. 6, 2026.
U.S. Appl. No. 18/095,968, filed Jan. 11, 2023 Non-Final Office Action dated Mar. 23, 2026.
U.S. Appl. No. 18/410,781, filed Jan. 11, 2024 Non-Final Office Action dated Mar. 25, 2026.

* cited by examiner 102
110
194
188
182
188
186
184
184
108
100

190
166
206
185
148,162
192
180
178

158
142
140
160
146
106
172
176
174
170
168
185
180
178

142
140
196
160
146

106
198
200
192
148,162
104

106
198
200
200
148,162
104

198
200
202
204
206
104
106
192

106
190
178
186
203
148,162
198
104
178

104
178
186
190
203
106
178

145
164
148, 162
104

160
146
162
142

160
148
156
140

148
156
152
154

PROXIMAL
112
122
24
24
138
136
124
23
23
120
126
134
DISTAL 132
122
130
128

128
120
124

VALVE MODULES AND METHODS FOR INTRODUCER ASSEMBLIES AND RAPIDLY INSERTABLE CENTRAL-CATHETER INSERTION ASSEMBLIES

PRIORITY

This application claims the benefit of priority to U.S. Provisional Patent Application No. 63/405,784, filed Sep. 12, 2022, which is incorporated by reference in its entirety into this application.

BACKGROUND

Central venous catheter ("CVCs") are commonly introduced into patients and advanced through their vasculatures by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps are time consuming, handling the number of medical devices is awkward, and both of the foregoing can lead to patient trauma. In addition, there is a relatively high potential for touch contamination due to the number of medical devices that need to be interchanged during the Seldinger technique. As such, there is a need to reduce the number of steps and medical devices involved in introducing a catheter such as a CVC into a patient and advancing the catheter through a vasculature thereof.

Disclosed herein are valve modules and methods for insertion assemblies and rapidly insertable central-catheter ("RICC") insertion assemblies that address the foregoing need.

SUMMARY

Disclosed herein is a RICC insertion assembly including, in some embodiments, a RICC, an introducer needle, a coupler coupling the RICC and the introducer needle together, and an access guidewire disposed in the introducer needle. The introducer needle includes a needle shaft and a sheath over the needle shaft. The needle shaft includes a longitudinal needle slot extending from a proximal portion of the needle shaft through a distal needle tip. The sheath over the needle shaft seals the needle slot thereunder except for a portion of the needle slot under a sheath opening in a proximal portion of the sheath. The coupler includes a coupler housing and a valve module disposed in a valve-module compartment of the coupler housing. The valve module includes an elastomeric gasket encircling at least a portion of the valve-module compartment of the coupler housing along a length of the valve-module compartment. The gasket in the valve-module compartment is compressed around a proximal portion of the introducer needle in a ready-to-deploy state of the RICC insertion assembly, thereby creating a substantially air-tight space within the gasket around the proximal portion of the introducer needle. The access guidewire includes a distal portion passing into the introducer needle through both the sheath opening of the sheath and the needle slot of the needle shaft. The gasket in the valve-module compartment is also compressed around the distal portion of the access guidewire in the ready-to-deploy state of the RICC insertion assembly, thereby further creating the substantially air-tight space within the gasket around the distal portion of the access guidewire. The access guidewire also includes a distal end disposed in the introducer needle just proximal of a needle tip in a distal end of the introducer needle.

In some embodiments, the gasket is formed of a unitary piece.

In some embodiments, the gasket includes a proximal needle through-hole through a proximal-end portion of the gasket and a distal needle through-hole aligned with the proximal needle through-hole through a distal-end portion of the gasket. The proximal portion of the introducer needle passes through both the proximal needle through-hole and the distal needle through-hole in the ready-to-deploy state of the RICC insertion assembly.

In some embodiments, the gasket includes an access-guidewire channel through the proximal-end portion of the gasket. The access-guidewire channel forms an acute angle with the proximal needle through-hole, thereby directing the distal portion of the access guidewire into the proximal portion of the introducer needle through both the sheath opening of the sheath and the needle slot of the needle shaft.

In some embodiments, the access-guidewire channel is coincident with a terminal portion of a longitudinal slit through a top portion of the gasket.

In some embodiments, the access-guidewire channel has an inner diameter commensurate with an outer diameter of the access guidewire.

In some embodiments, the distal needle through-hole is coincident with another terminal portion of the slit through the top portion of the gasket.

In some embodiments, the distal needle through-hole has an inner diameter commensurate with an outer diameter of the introducer needle.

In some embodiments, the slit is configured to separate and allow the access guidewire to escape from the top portion of the gasket when compression on the gasket is relieved and the introducer needle is withdrawn from the coupler.

In some embodiments, the gasket is formed of two complementary pieces of the gasket mated together.

In some embodiments, the gasket is substantially symmetric along a longitudinal plane of symmetry through a majority of the gasket. The two complementary pieces of the gasket substantially are mirror images of each other.

In some embodiments, the gasket is asymmetric. The two complementary pieces of the gasket are not related to each other by any symmetry operation.

In some embodiments, the gasket includes a proximal needle through-hole through a proximal-end portion of the gasket and a distal needle through-hole aligned with the proximal needle through-hole through a distal-end portion of the gasket. Each through-hole of the proximal needle through-hole and the distal needle through-hole is formed between the two complementary pieces of the gasket mated together. The proximal portion of the introducer needle passes through both the proximal needle through-hole and the distal needle through-hole in the ready-to-deploy state of the RICC insertion assembly.

In some embodiments, the gasket includes an access-guidewire channel through the proximal-end portion of the gasket. The access-guidewire channel is formed between the two complementary pieces of the gasket mated together. The access-guidewire channel forms an acute angle with the proximal needle through-hole, thereby directing the distal portion of the access guidewire into the introducer needle through both the sheath opening of the sheath and the needle slot of the needle shaft.

In some embodiments, the two complementary pieces of the gasket are configured to separate and allow the access guidewire to escape from the gasket when compression on the gasket is relieved and the introducer needle is withdrawn from the coupler.

In some embodiments, the gasket approximates a rectangle in a side-on view of the gasket.

In some embodiments, the gasket approximates a right trapezoid in a side-on view of the gasket.

In some embodiments, the coupler further includes a blade coupled to the coupler housing. The blade extends into the valve module through the gasket such that a distal facing blade edge is disposed in the needle slot of the needle shaft under a distal end of the sheath opening of the sheath for cutting the sheath off the needle shaft as the introducer needle is withdrawn from the coupler. Cutting the sheath off the needle shaft allows the access guidewire to escape from the needle shaft through the needle slot.

In some embodiments, the coupler housing includes a longitudinal coupler-housing slot configured to allow the access guidewire to escape from the coupler housing when the introducer needle is withdrawn from the coupler.

In some embodiments, the coupler further includes a compression clip over complementary mated pieces of the coupler housing. The compression clip is configured to compress the gasket in the valve-module compartment.

In some embodiments, the coupler further includes one or more lubricant wells including a lubricant, one or more lubricant receptors configured to receive or redistribute the lubricant, or a combination thereof.

In some embodiments, the RICC insertion assembly further includes a syringe fluidly coupled to the introducer needle in the ready-to-deploy state of the RICC insertion assembly.

Also disclosed herein is a valve module for a RICC insertion assembly including, in some embodiments, an elastomeric gasket. The elastomeric gasket is configured to encircle at least a portion of a valve-module compartment of a coupler housing of a coupler along a length of the valve-module compartment. The elastomeric gasket is also configured to compress in the valve-module compartment of the coupler housing around a proximal portion of an introducer needle and a distal portion of an access guidewire, thereby creating a substantially air-tight space within the gasket around the proximal portion of the introducer needle and the distal portion of the access guidewire.

In some embodiments, the gasket is formed of a unitary piece.

In some embodiments, the gasket includes a proximal needle through-hole through a proximal-end portion of the gasket and a distal needle through-hole aligned with the proximal needle through-hole through a distal-end portion of the gasket. Both the proximal needle through-hole and the distal needle through-hole are configured to accept therethrough the proximal portion of the introducer needle.

In some embodiments, the gasket includes an access-guidewire channel through the proximal-end portion of the gasket. The access-guidewire channel forms an acute angle with the proximal needle through-hole, thereby directing the distal portion of the access guidewire into the proximal portion of the introducer needle through an opening in a side of the introducer needle.

In some embodiments, the access-guidewire channel is coincident with a terminal portion of a longitudinal slit through a top portion of the gasket.

In some embodiments, the distal needle through-hole is coincident with another terminal portion of the slit through the top portion of the gasket.

In some embodiments, the gasket is formed of two complementary pieces of the gasket mated together.

In some embodiments, the gasket is substantially symmetric along a longitudinal plane of symmetry through a majority of the gasket. The two complementary pieces of the gasket substantially are mirror images of each other.

In some embodiments, the gasket is asymmetric. The two complementary pieces of the gasket are not related to each other by any symmetry operation.

In some embodiments, the gasket includes a proximal needle through-hole through a proximal-end portion of the gasket and a distal needle through-hole aligned with the proximal needle through-hole through a distal-end portion of the gasket. Each through-hole of the proximal needle through-hole and the distal needle through-hole is formed between the two complementary pieces of the gasket mated together. Both the proximal needle through-hole and the distal needle through-hole are configured to accept therethrough the proximal portion of the introducer needle.

In some embodiments, the gasket includes an access-guidewire channel through the proximal-end portion of the gasket. The access-guidewire channel is formed between the two complementary pieces of the gasket mated together. The access-guidewire channel forms an acute angle with the proximal needle through-hole, thereby directing the distal portion of the access guidewire into the introducer needle through an opening in a side of the introducer needle.

In some embodiments, the gasket approximates a rectangle in a side-on view of the gasket.

In some embodiments, the gasket approximates a right trapezoid in a side-on view of the gasket.

In some embodiments, the gasket is further configured to accept a blade therethrough such that the blade extends into the valve module for cutting a sheath off a needle shaft of the introducer needle when the introducer needle is withdrawn from the coupler.

Also disclosed herein is a method for inserting a RICC into a blood-vessel lumen of a patient including, in some embodiments, a RICC insertion assembly-obtaining step, a needle tract-establishing step, an access guidewire-advancing step, an introducer needle-withdrawing step, and a RICC-advancing step. The RICC insertion assembly-obtaining step includes obtaining a RICC insertion assembly including the RICC, an introducer needle including a sheath over a needle shaft, and an access guidewire coupled together by a coupler. The coupler includes a coupler housing having a valve-module compartment and a valve module disposed in the valve-module compartment. The valve module includes an elastomeric gasket encircling at least a portion of the valve-module compartment of the coupler housing along a length of the valve-module compartment. The gasket in the valve-module compartment of the coupler housing is compressed around a proximal portion of the introducer needle and a distal portion of the access guidewire in a ready-to-deploy state of the RICC insertion assembly, thereby creating a substantially air-tight space within the gasket around the proximal portion of the introducer needle and the distal portion of the access guidewire. The needle tract-establishing step includes establishing a needle tract from an area of skin to the blood-vessel lumen with the introducer needle. The access guidewire-advancing step includes advancing a distal end of the access guidewire from its initial location in the needle shaft just proximal of a needle tip of the needle shaft into the blood-vessel lumen. The introducer needle-withdrawing step includes withdrawing the introducer needle from the coupler leaving the access guidewire in place in the blood-vessel lumen. The introducer needle further includes a longitudinal needle slot extending from a proximal portion of the needle shaft through the needle tip. The gasket includes a longitudinal slit in at least a top portion of the gasket, thereby allowing the access guidewire to escape from the introducer needle and the gasket, respectively, with the withdrawing of the introducer needle from the coupler. The RICC-advancing step includes advancing a catheter tube of the RICC over the access guidewire and into the blood-vessel lumen, thereby inserting the RICC into the blood-vessel lumen.

In some embodiments, the method further includes a blood-aspirating step. The blood-aspirating step includes aspirating blood with a syringe fluidly connected to the introducer needle for confirmation the needle tract extends into the blood-vessel lumen before performing the introducer needle-withdrawing step. The sheath over the needle shaft seals the needle slot thereunder except for a portion of the needle slot under a sheath opening of the sheath, which portion of the needle slot is sealed by the substantially air-tight space within the gasket for the aspirating of the blood with the syringe.

In some embodiments, the introducer needle-withdrawing step further includes withdrawing the introducer needle from the gasket. The gasket includes a proximal needle through-hole through a proximal-end portion of the gasket and a distal needle through-hole aligned with the proximal needle through-hole through a distal-end portion of the gasket.

In some embodiments, the access guidewire-advancing step further includes advancing the access guidewire into an access-guidewire channel through the proximal-end portion of the gasket. The access-guidewire channel forms an acute angle with the proximal needle through-hole, thereby directing the distal portion of the access guidewire into the needle slot of the introducer needle.

In some embodiments, the gasket is formed of two complementary, substantially mirror-imaged pieces of the gasket mated together. The two complementary pieces of the gasket form the proximal needle through-hole, the distal needle through-hole, and the access-guidewire channel across a longitudinal plane of symmetry between the two complementary pieces of the gasket mated together. The plane of symmetry is coincident with and continues the slit in at least the top portion of the gasket through a bottom portion of the gasket.

In some embodiments, the gasket is formed of a unitary piece including the slit through the top portion of the gasket.

In some embodiments, the introducer needle-withdrawing step further includes simultaneously cutting the sheath off the needle shaft with the access guidewire, itself, or a blade extending into the valve module through the gasket while the introducer needle is withdrawn from the coupler. The cutting of the sheath off the needle shaft allows the access guidewire to escape from the needle shaft by way of the needle slot thereof.

Also disclosed herein is an introducer assembly including, in some embodiments, an introducer needle, a coupler, and an access guidewire. The introducer needle includes a needle shaft and a sheath over the needle shaft. The needle shaft includes a longitudinal needle slot extending from a proximal portion of the needle shaft through a distal needle tip. The sheath over the needle shaft seals the needle slot thereunder except for a portion of the needle slot under a sheath opening in a proximal portion of the sheath. The coupler includes a coupler housing and a valve module disposed in a valve-module compartment of the coupler housing. The valve module includes an elastomeric gasket encircling at least a portion of the valve-module compartment of the coupler housing along a length of the valve-module compartment. The gasket in the valve-module compartment is compressed around a proximal portion of the introducer needle in a ready-to-deploy state of the introducer assembly, thereby creating a substantially air-tight space within the gasket around the proximal portion of the introducer needle. The access guidewire includes a distal portion passing into the introducer needle through both the sheath opening of the sheath and the needle slot of the needle shaft. The gasket in the valve-module compartment is also compressed around the distal portion of the access guidewire in the ready-to-deploy state of the introducer assembly, thereby further creating the substantially air-tight space within the gasket around the distal portion of the access guidewire. The access guidewire also includes a distal end disposed in the introducer needle just proximal of a needle tip in a distal end of the introducer needle.

In some embodiments, the introducer assembly further includes a syringe fluidly coupled to the introducer needle in the ready-to-deploy state of the introducer assembly.

Also disclosed herein is a method for establishing access to a blood-vessel lumen of a patient including, in some embodiments, an introducer assembly-obtaining step, a needle tract-establishing step, an access guidewire-advancing step, and an introducer needle-withdrawing step. The introducer assembly-obtaining step includes obtaining an introducer assembly including an introducer needle having a sheath over a needle shaft, an access guidewire, and a coupler coupling together the introducer needle and the access guidewire. The coupler includes a coupler housing having a valve-module compartment and a valve module disposed in the valve-module compartment. The valve module includes an elastomeric gasket encircling at least a portion of the valve-module compartment of the coupler housing along a length of the valve-module compartment. The gasket in the valve-module compartment of the coupler housing is compressed around a proximal portion of the introducer needle and a distal portion of the access guidewire in a ready-to-deploy state of the introducer assembly, thereby creating a substantially air-tight space within the gasket around the proximal portion of the introducer needle and the distal portion of the access guidewire. The needle tract-establishing step includes establishing a needle tract from an area of skin to the blood-vessel lumen with the introducer needle. The access guidewire-advancing step includes advancing a distal end of the access guidewire from its initial location in the needle shaft just proximal of a needle tip of the needle shaft into the blood-vessel lumen. The introducer needle-withdrawing step includes withdrawing the introducer needle from the coupler leaving the access guidewire in place in the blood-vessel lumen. The introducer needle further includes a longitudinal needle slot extending from a proximal portion of the needle shaft through the needle tip. The gasket includes a longitudinal slit in at least a top portion of the gasket, thereby allowing the access guidewire to escape from the introducer needle and the gasket, respectively, with the withdrawing of the introducer needle from the coupler.

In some embodiments, the method further includes a catheter-threading step and a catheter-advancing step. The catheter-threading step includes threading a catheter tube of a CVC over a proximal portion of the access guidewire. The catheter-advancing step includes advancing the catheter tube of the CVC over the access guidewire and into the blood-vessel lumen.

In some embodiments, the method further includes a dilating step. The dilating step includes dilating tissue around the needle tract with a dilator before the threading of the catheter tube of the CVC over the proximal portion of the access guidewire in the catheter-threading step.

These and other features of the concepts provided herein will become more apparent to those of skill in the art in view of the accompanying drawings and following description, which describe particular embodiments of such concepts in greater detail.

DRAWINGS

DESCRIPTION

Figure 1:
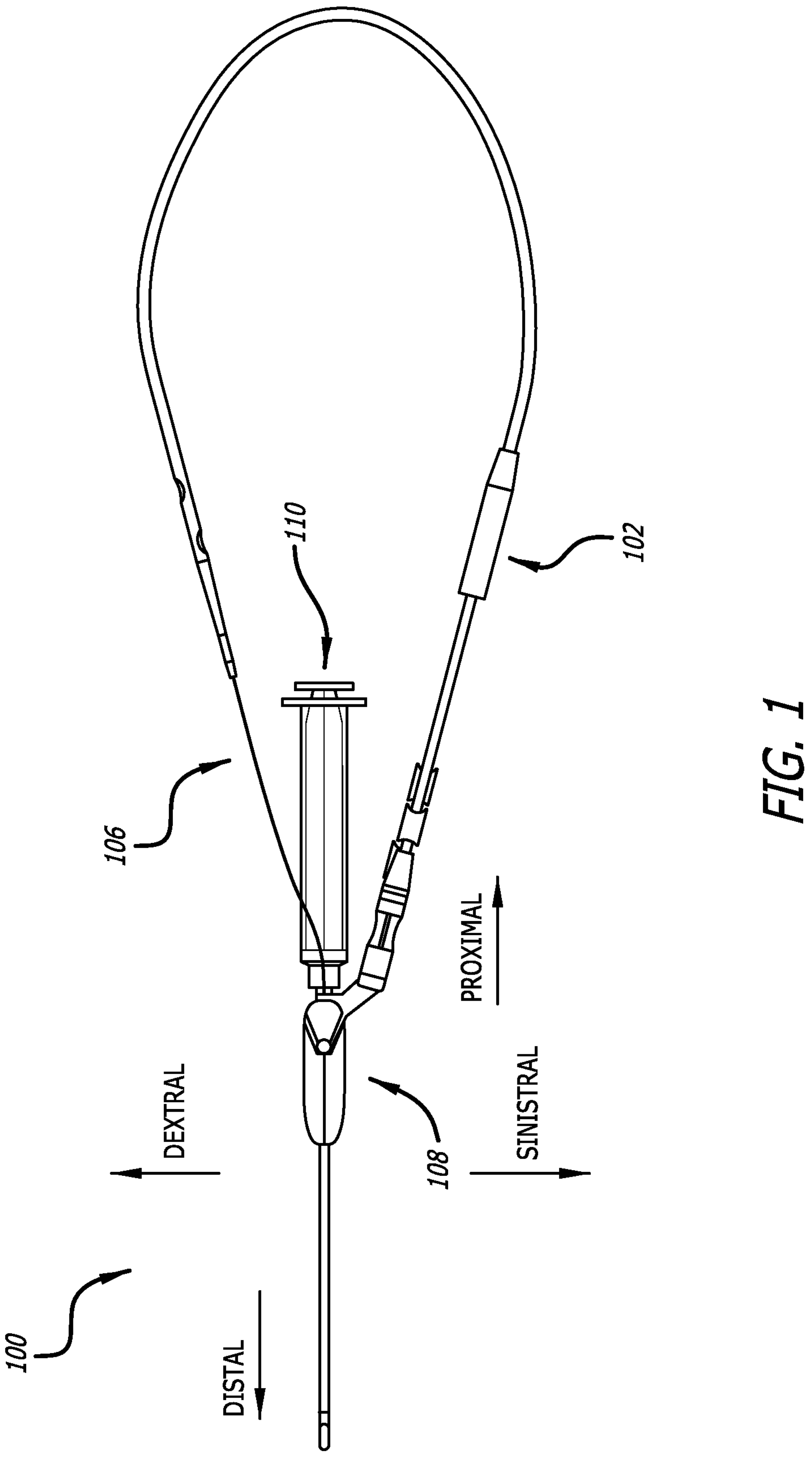
FIG. 1 illustrates a top view of a RICC insertion assembly in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or "proximal section" of, for example, a medical device includes a portion or section of the medical device intended to be near a clinician when the medical device is used on a patient. Likewise, a "proximal length" of the medical device includes a length of the medical device intended to be near the clinician when the medical device is used on the patient. A "proximal end" of the medical device is an end of the medical device intended to be near the clinician when the medical device is used on the patient. The proximal portion, the proximal section, or the proximal length of the medical device can include the proximal end of the medical device, and, in such instances, the proximal portion, the proximal section, or the proximal length of the medical device can be further specified as a "proximal-end portion," a "proximal-end section," or a "proximal-end length" of the medical device. That said, the proximal portion, the proximal section, or the proximal length of the medical device need not include the proximal end of the medical device. Indeed, unless context suggests otherwise, the proximal portion, the proximal section, or the proximal length of the medical device is not a terminal portion, terminal section, or terminal length of the medical device.

With respect to "distal," a "distal portion" or "distal section" of, for example, a medical device includes a portion or section of the medical device intended to be near or in a patient when the medical device is used on the patient. Likewise, a "distal length" of the medical device includes a length of the medical device intended to be near or in the patient when the medical device is used on the patient. A "distal end" of the medical device is an end of the medical device intended to be near or in the patient when the medical device is used on the patient. The distal portion, the distal section, or the distal length of the medical device can include the distal end of the medical device, and, in such instances, the distal portion, the distal section, or the distal length of the medical device can be further specified as a "distal-end portion," a "distal-end section," or a "distal-end length" of the medical device. That said, the distal portion, the distal section, or the distal length of the medical device need not include the distal end of the medical device. Indeed, unless context suggests otherwise, the distal portion, the distal section, or the distal length of the medical device is not a terminal portion, terminal section, or terminal length of the medical device.

Unless defined otherwise, all technical and scientific terms used herein have the same meaning as commonly understood by those of ordinary skill in the art.

As set forth above with respect to the Seldinger technique, performing the number of steps of the Seldinger technique is time consuming, handling the number of medical devices of the Seldinger technique is awkward, and both of the foregoing can lead to patient trauma. In addition, there is a relatively high potential for touch contamination due to the number of medical devices that need to be interchanged during the Seldinger technique. As such, there is a need to reduce the number of steps and medical devices involved in introducing a catheter such as a CVC into a patient and advancing the catheter through a vasculature thereof.

Disclosed herein are valve modules and methods for insertion assemblies and RICC insertion assemblies that address the foregoing need. The valve modules for the RICC insertion assemblies and the methods thereof will become more apparent to those of skill in the art in view of the accompanying drawings and following description, which provide particular embodiments of the valve modules as they relate to the RICC insertion assemblies provided herein. However, it should be understood that the valve modules can be incorporated into other medical devices including other catheter insertion assemblies than the RICC insertion assemblies provided herein. Indeed, the valve modules can be incorporated into catheter insertion assemblies including peripherally inserted central catheters ("PICCs"), dialysis catheters, or the like.

RICC Insertion Assemblies

Figure 2:
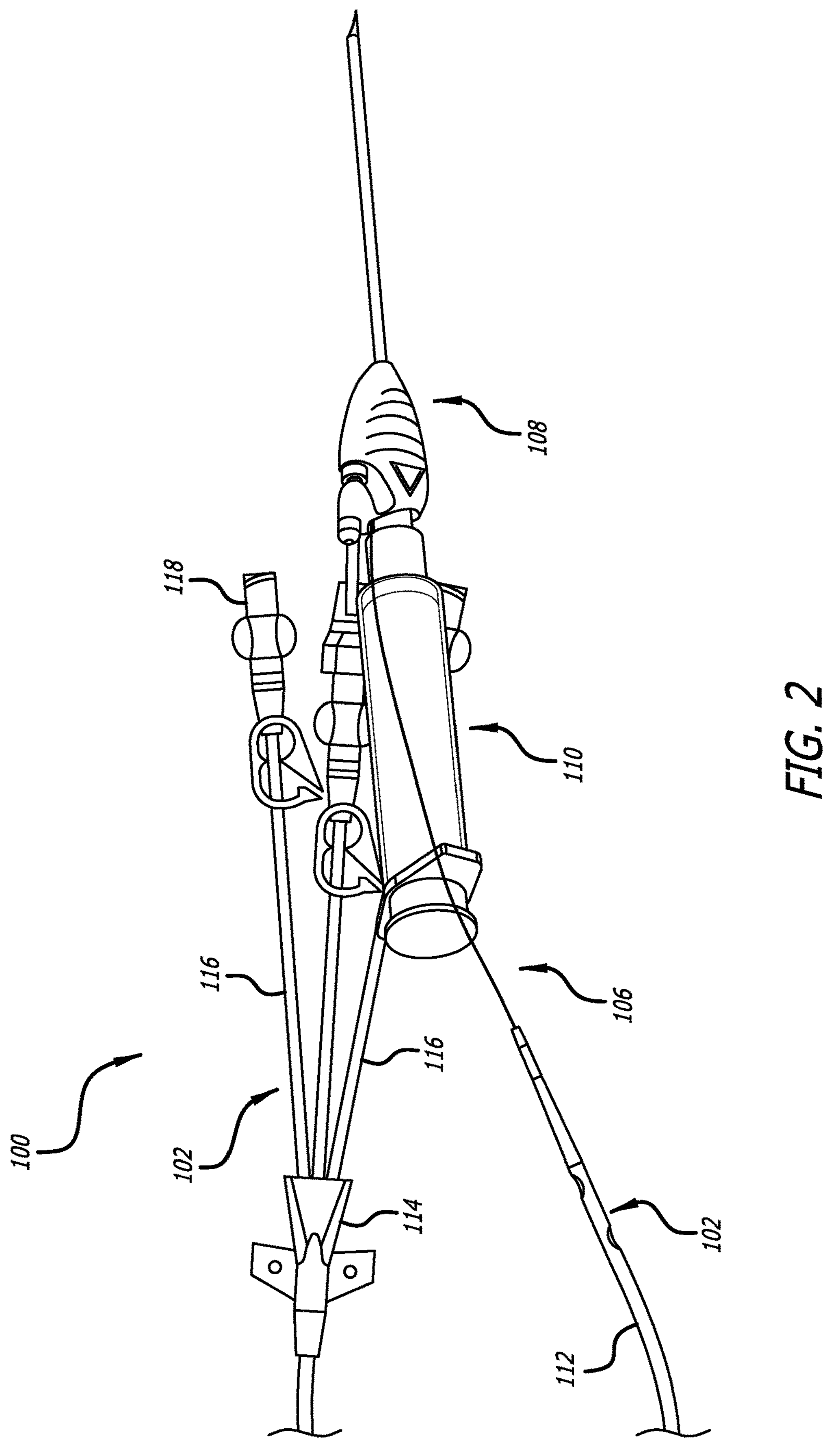
FIG. 2 illustrates a perspective view of the RICC insertion assembly in accordance with some embodiments.
Figure 3:
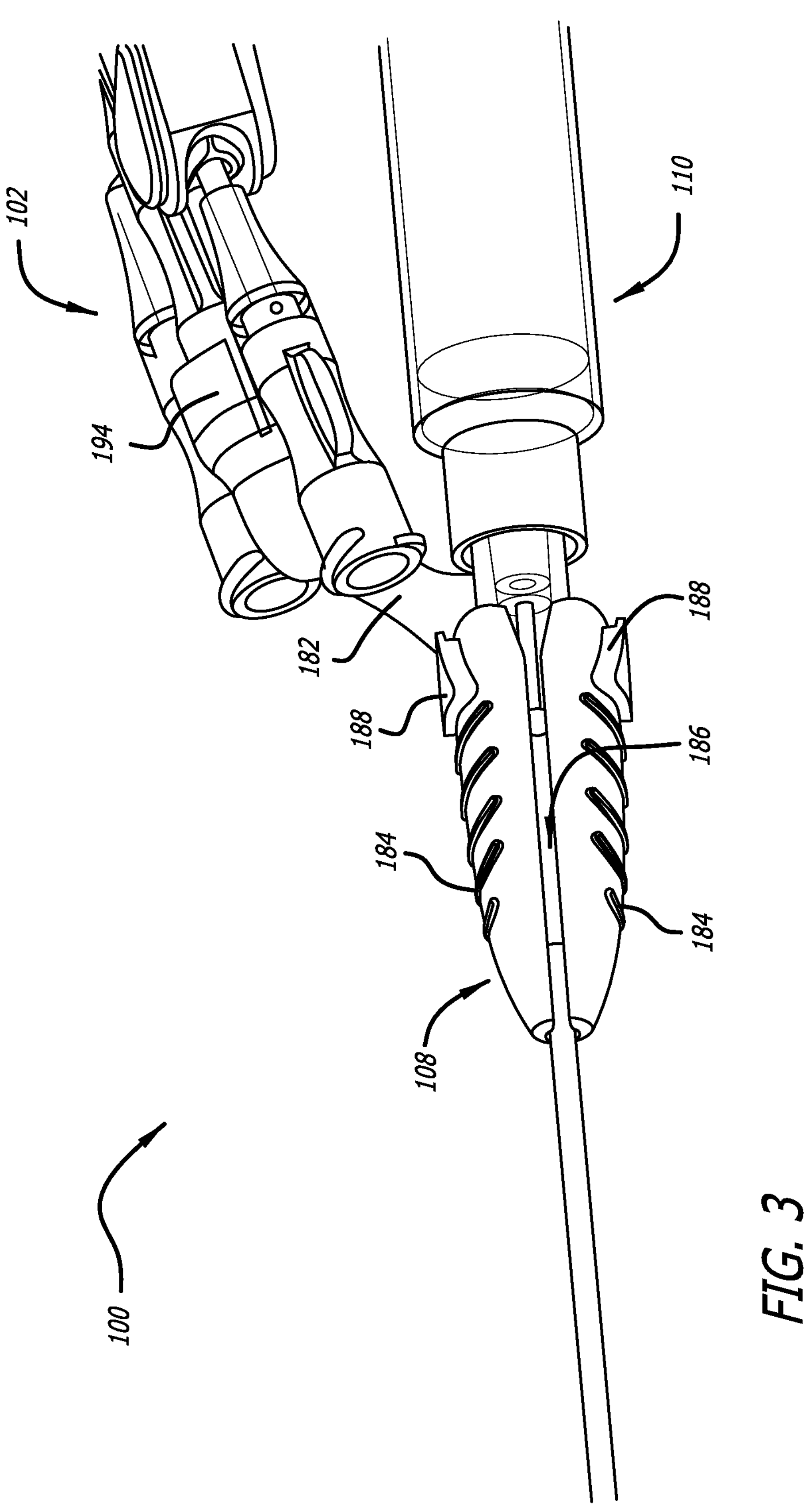
FIG. 3 illustrates a bottom view of the RICC insertion assembly in accordance with some embodiments.

FIGS. 1-3 illustrate various views of a RICC insertion assembly 100 in accordance with some embodiments.

As shown, the RICC insertion assembly 100 can include a RICC 102, an introducer needle 104, an access guidewire 106, and a coupler 108 coupling the RICC 102, the introducer needle 104, and the access guidewire 106 together in a ready-to-deploy state of the RICC insertion assembly 100. Notably, the proximal end of the access guidewire 106 can be coupled to the coupler 108 and the distal end of the access guidewire 106 can be disposed in the needle lumen 158 of the introducer needle 104 as set forth below. This enforces a loop in the access guidewire 106, which loop the RICC 102 can be disposed over in the ready-to-deploy state of the RICC insertion assembly 100 keeping the RICC insertion assembly 100 in a relatively compact form.

The RICC insertion assembly 100 can further include a syringe 110 fluidly coupled to the introducer needle 104 in the ready-to-deploy state of the RICC insertion assembly 100. As set forth below, the sheath 142 can seal the needle slot 148 of the needle shaft 140. In particular, the sheath 142 can seal the needle slot 148 outside of the valve module 180. The valve module 180 or the gasket 198 thereof, in turn, can seal over the sheath opening 162 of the sheath 142 that opens to the needle slot 148. The valve module 180 or the gasket 198 thereof can also seal around the access guidewire 106. Such seals enable the syringe 110 to aspirate blood in accordance with the blood-aspirating step of the method set forth below.

Lastly, any component of the RICC insertion assembly 100 selected from at least the RICC 102, the introducer needle 104, the access guidewire 106, the coupler 108, and the syringe 110, or any portion of the component selected from the foregoing components, can include an antimicrobial thereon or therein. In an example, the catheter tube 112 of the RICC 102 can include an antimicrobial coating on an abluminal surface of the catheter tube 112, a luminal surface of the catheter tube 112, or both. In another example, a pre-extrusion material of the catheter tube 112 can include the antimicrobial admixed therein such that the antimicrobial is incorporated into the catheter tube 112 when extruded, the antimicrobial protecting both the abluminal surface of the catheter tube 112 and the luminal surface of the catheter tube 112 from microbial contamination.

Figure 21:
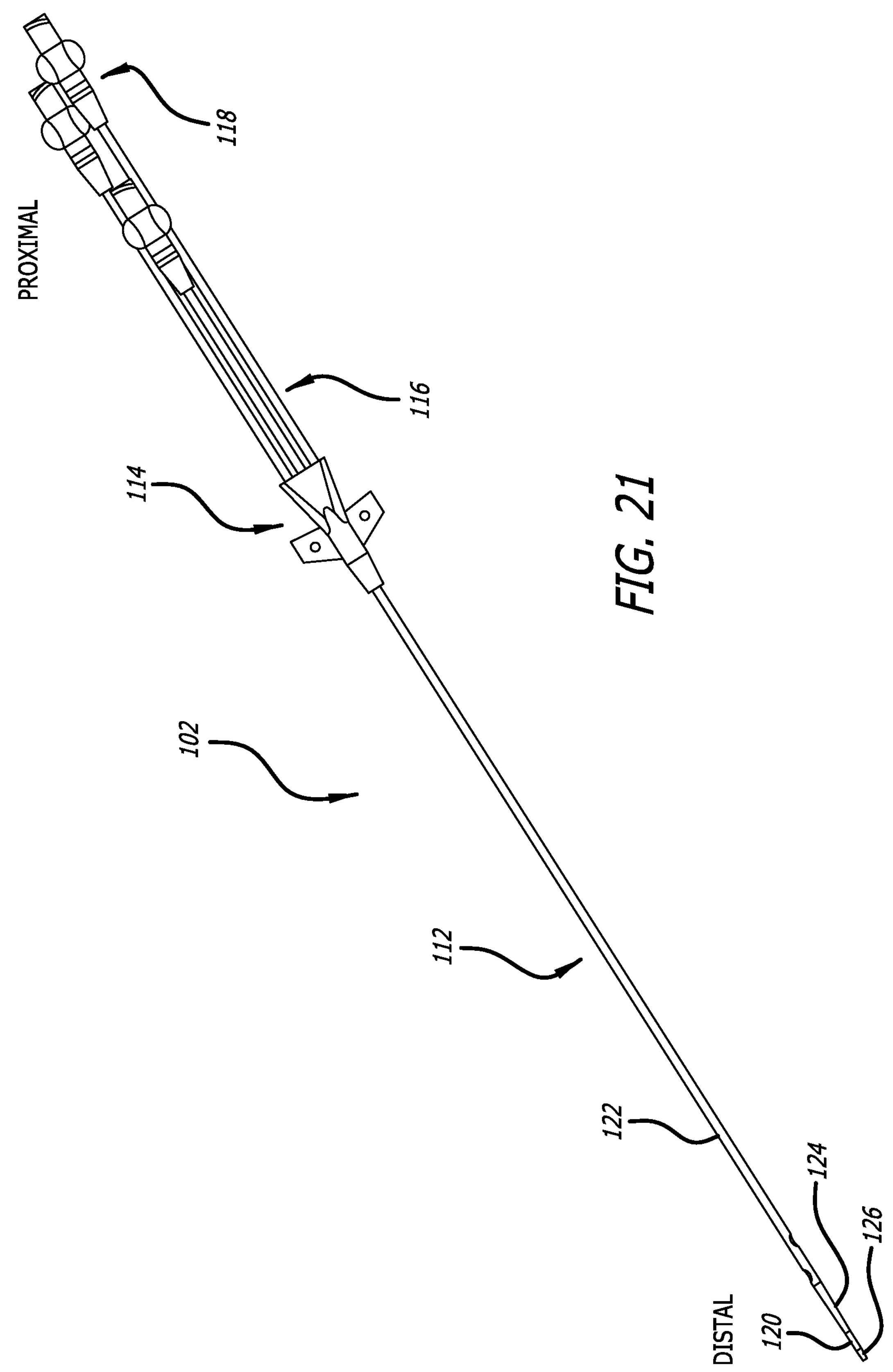
FIG. 21 illustrates a RICC of the RICC insertion assembly in accordance with some embodiments.

FIG. 21 illustrates the RICC 102 of the RICC insertion assembly 100 in accordance with some embodiments.

As shown, the RICC 102 can include a catheter tube 112, a catheter hub 114, one or more extension legs 116, and one or more extension-leg connectors 118.

FIGS. 22-25 illustrate various views of the catheter tube 112 of the RICC 102 in accordance with some embodiments.

The catheter tube 112 can include a first section 120 in a distal portion of the catheter tube 112, a second section 122 in the distal portion of the catheter tube 112 proximal of the first section 120, and a tapered junction 124 between the first and second sections 120 and 122 of the catheter tube 112.

Figure 25:
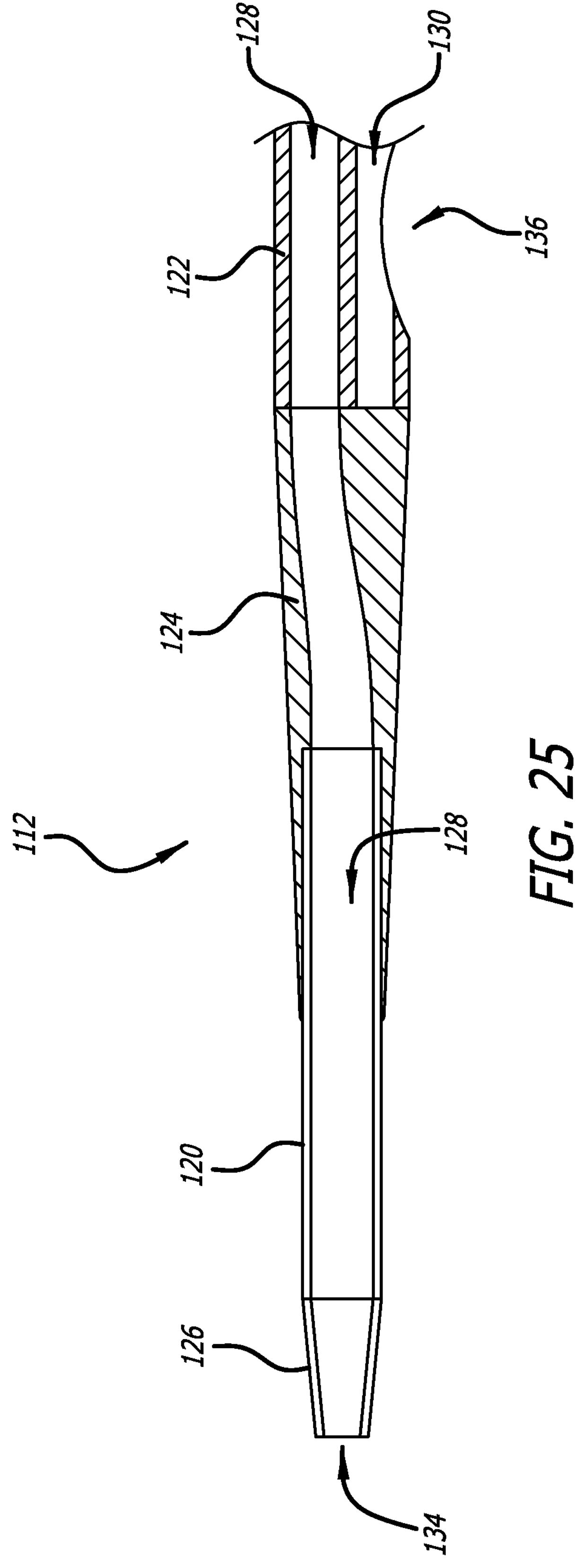
FIG. 25 illustrates a longitudinal cross section of the distal portion of the catheter tube in accordance with some embodiments.

The first section 120 of the catheter tube 112 can include a catheter tip 126 having a relatively short taper from an outer diameter of a distal portion of the first section 120 distal of the junction 124 to an outer diameter of a distal end of the first section 120. The taper of the catheter tip 126 can be configured for immediate dilation of tissue about a needle tract established with the introducer needle 104 up to the outer diameter of the distal portion of the first section 120 of the catheter tube 112. As best shown in FIG. 25, the first section 120 of the catheter tube 112 can also include a proximal portion disposed in a bore of a distal portion of the junction 124 and fixedly coupled thereto such as by a solvent bond, an adhesive bond, or a heat weld.

The second section 122 of the catheter tube 112 can include a consistent outer diameter over its length from a distal end of the second section 122 to a proximal end of the second section 122. The consistent diameter of the second section 122 of the catheter tube 112 can be configured for smooth insertion into the needle tract and targeted vasculature subsequent to any dilation by the first section 120 of the catheter tube 112 and the junction 124. The distal end of the second section 122 of the catheter tube 112 can have a flat face flush with the flat-faced proximal end of the junction 124 and fixedly coupled thereto such as by a solvent bond, an adhesive bond, or a heat weld.

The junction 124 can include a taper over its length from a proximal end of the junction 124 to a distal end of the junction 124. The taper of the junction 124 can be configured for immediate dilation of the tissue about the needle tract from the outer diameter of the proximal portion of the first section 120 of the catheter tube 112 to the outer diameter of the second section 122 of the catheter tube 112. An abluminal surface of the junction 124 can smoothly transition from an abluminal surface of the first section 120 of the catheter tube 112 to an abluminal surface of the second section 122 of the catheter tube 112 without edges that catch on skin when the catheter tube 112 is inserted into the needle tract. In addition to the edges being minimal to negligible, the edges can include solvent-interdiffused polymeric material of the polymeric materials from which the catheter tube 112 is formed, which smoothens the transitions from the first section 120 of the catheter tube 112 to the junction 124 and from the junction 124 to the second section 122 of the catheter tube 112. Notably, the junction 124 can have a length approximately commensurate with a length of an exposed portion of the first section 120 of the catheter tube 112 or between lengths of exposed portions of the first and second sections 120 and 122 of the catheter tube 112. As such, the length of the exposed portion of the first section 120 of the catheter tube 112 can be less than the length of the junction 124 up to approximately commensurate with the length of the junction 124.

The first section 120 of the catheter tube 112 can be formed of a first polymeric material (e.g., a polytetrafluoroethylene, a polypropylene, or a polyurethane) having a first durometer. The second section 122 of the catheter tube 112 can be formed of a second polymeric material (e.g., a polyvinyl chloride, a polyethylene, another polyurethane, or a silicone) having a second durometer less than the first durometer. For example, the first section 120 of the catheter tube 112 can be formed of a first polyurethane having the first durometer while the second section 122 of the catheter tube 112 can be formed of a second, different polyurethane (e.g., a same or different diisocyanate or triisocyanate reacted with a different diol or triol, a different diisocyanate or triisocyanate reacted with a same or different diol or triol, a same diisocyanate or triisocyanate reacted with a same diol or triol under different conditions or with different additives, etc.) having the second durometer less than the first durometer. Indeed, polyurethanes are advantageous for the catheter tube 112 in that polyurethanes can be relatively rigid at room-temperature but become more flexible in vivo at body temperature, which reduces irritation to vessel walls as well as phlebitis. Polyurethanes are also advantageous in that they can be less thrombogenic than some other polymers. The junction 124 can be formed of the second polymeric material or a third polymeric material (e.g., yet another polyurethane) having a third durometer less than the first durometer and greater than, approximately equal to, or less than the second durometer.

It should be understood the first durometer of the first polymeric material, the second durometer of the second polymeric material, and the third durometer of the third polymeric material can be on different scales (e.g., Type A or Type D). With this understanding, the second durometer of the second polymeric material or the third durometer of the third polymeric material might not be numerically less than the first durometer of the first polymeric material when the second durometer or the third durometer is less than the first durometer. Indeed, the hardness of the second polymeric material or the third polymeric material can still be less than the hardness of the first polymeric material as the different scales—each of which ranges from 0 to 100—are designed for characterizing different materials in groups of the materials having a like hardness.

In accordance with the first section 120 of the catheter tube 112, the second section 122 of the catheter tube 112, and the junction 124 between the first and second sections 120 and 122 of the catheter tube 112 set forth above, the catheter tube 112 can possess a column strength sufficient to prevent buckling of the catheter tube 112 when inserted into a needle tract established by with the introducer needle 104. The column strength of the catheter tube 112 can also be sufficient to prevent buckling of the catheter tube 112 when advanced through a vasculature of a patient without dilation of tissue about the needle tract or any blood vessels of the vasculature beforehand with a separate dilator.

Figures 22, 23, 24:
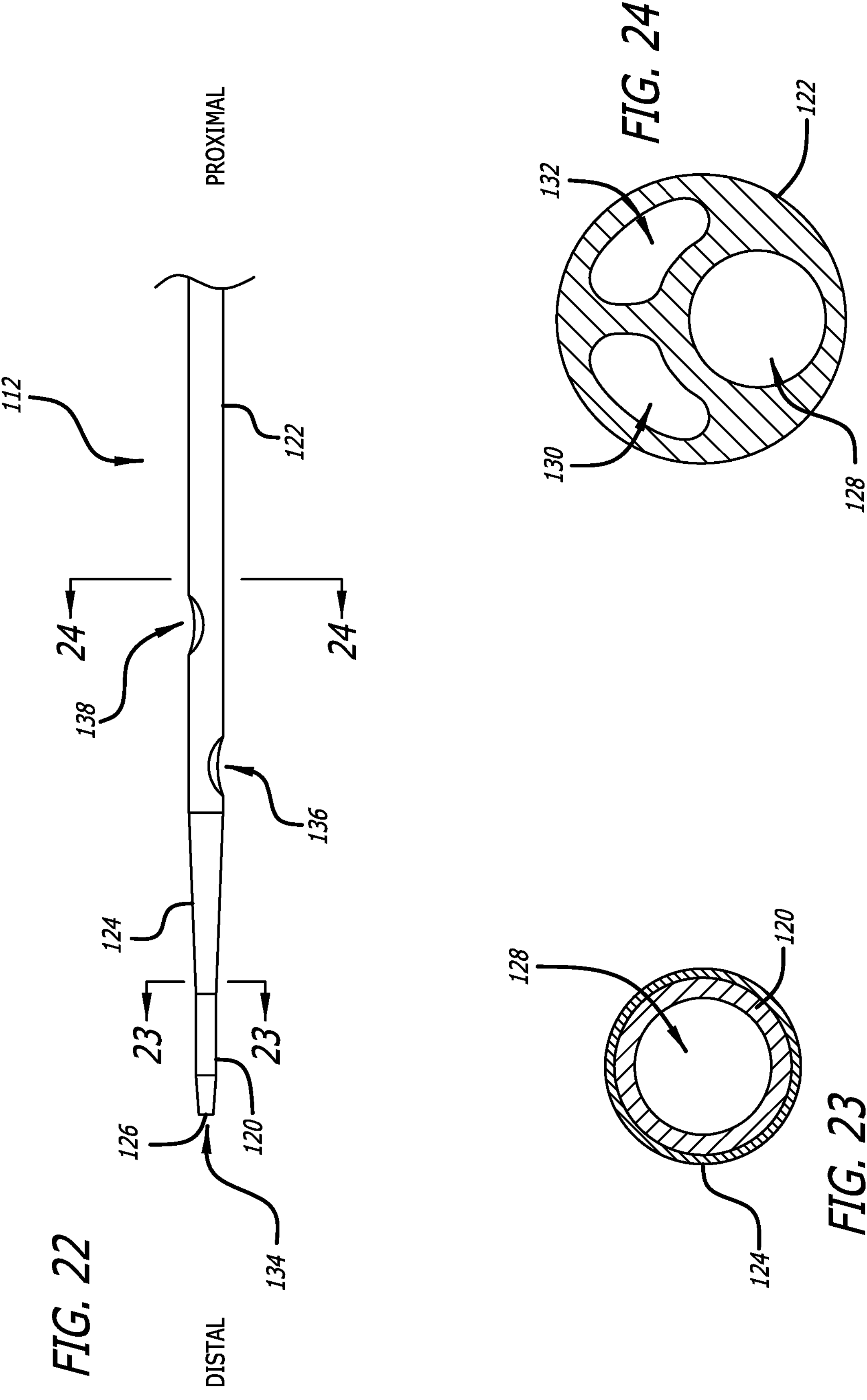
FIG. 22 illustrates a detailed view of a distal portion of a catheter tube of the RICC in accordance with some embodiments.
FIG. 23 illustrates a transverse cross section of the distal portion of the catheter tube in accordance with some embodiments.
FIG. 24 illustrates another transverse cross section of the distal portion of the catheter tube in accordance with some embodiments.

The catheter tube 112 can include one or more catheter-tube lumens extending through the catheter tube 112; however, only one catheter-tube lumen typically extends from a proximal end of the catheter tube 112 to a distal end of the catheter tube 112 in a multiluminal RICC (e.g., a diluminal RICC, a triluminal RICC, a tetraluminal RICC, a pentaluminal RICC, a hexaluminal RICC, etc.). (See FIGS. 22-25.) Indeed, the first section 120 of the catheter tube 112 typically includes a single lumen therethrough as shown in FIGS. 23 and 25.

The catheter hub 114 can be coupled to a proximal portion of the catheter tube 112. The catheter hub 114 can include one or more catheter-hub lumens corresponding in number to the one-or-more catheter-tube lumens. The one-or-more catheter-hub lumens can extend through an entirety of the catheter hub 114 from a proximal end of the catheter hub 114 to a distal end of the catheter hub 114.

Each extension leg of the one-or-more extension legs 116 can be coupled to the catheter hub 114 by a distal portion thereof. The one-or-more extension legs 116 can respectively include one or more extension-leg lumens, which, in turn, correspond in number to the one-or-more catheter-hub lumens. Each extension-leg lumen of the one-or-more extension-leg lumens can extend through an entirety of the extension leg from a proximal end of the extension leg to a distal end of the extension leg.

Each extension-leg connector of the one-or-more extension-leg connectors 118 can be over a proximal portion of an extension leg of the one-or-more extension legs 116. For example, each extension-leg connector of the one-or-more extension-leg connectors 118 can be a Luer connector over a proximal portion of an extension leg of the one-or-more extension legs 116. Through such an extension-leg connector, a corresponding extension leg and the extension-leg lumen thereof can be connected to another medical device and a lumen thereof. However, in the ready-to-deploy state of the RICC insertion assembly 100 at least one extension-leg connector (e.g., the extension-leg connector including part of the primary lumen 128 of the RICC 102) is typically connected to the swivel-arm connector 194 of the swivel arm 182 of the coupler 108 to enforce the loop in the access guidewire 106 and the RICC 102 thereover.

As shown, the RICC 102 can be a triluminal RICC including a set of three lumens; however, the RICC 102 is not limited to the set of the three lumens as set forth above. The set of three lumens can include a primary lumen 128, a secondary lumen 130, and a tertiary lumen 132 formed of fluidly connected portions of three catheter-tube lumens, three catheter-hub lumens, and three extension-leg lumens. The primary lumen 128 can have a primary-lumen aperture 134 in the distal end of the first section 120 of the catheter tube 112, which corresponds to the distal end of the catheter tube 112 and a distal end of the RICC 102. The secondary lumen 130 can have a secondary-lumen aperture 136 in a side of the distal portion of the catheter tube 112. The tertiary lumen 132 can have a tertiary-lumen aperture 138 in the side of the distal portion of the catheter tube 112 proximal of the secondary-lumen aperture 136.

FIGS. 4, 5, and 18-20 illustrate various views of the introducer needle 104 of the RICC insertion assembly 100 in accordance with some embodiments.

As shown, the introducer needle 104 can include a needle shaft 140, a sheath 142 over the needle shaft 140, and a needle hub 144 over both a proximal portion of the needle shaft 140 and a proximal portion of the sheath 142. In at least the ready-to-deploy state of the RICC insertion assembly 100, the needle shaft 140 and the sheath 142 can extend from the needle hub 144, through the valve module 180 or the gasket 198 thereof, and out a distal end of the coupler housing 178.

The needle shaft 140 can include a needle tip 146 in a distal portion of the needle shaft 140 and a longitudinal needle slot 148 extending from the proximal portion of the needle shaft 140 through the needle tip 146.

The needle tip 146 can include a bevel having a tip bevel 152 and a primary bevel 154 proximal of the tip bevel 152. A tip-bevel angle of the tip bevel 152 can be greater than a primary-bevel angle of the primary bevel 154 such that the bevel provides a smooth transition over the needle tip 146. Such a needle tip can thusly be configured for establishing a needle tract from an area of skin into a blood-vessel lumen of a patient in accordance with the needle tract-establishing step of the method set forth below.

The needle slot 148 can extend from at least the proximal portion of the needle shaft 140 through the needle tip 146, thereby forming a needle channel 156 along a majority up to an entirety of a length of the needle shaft 140 as opposed to a needle lumen therethrough. While the needle slot 148 is shown in a top portion of the needle shaft 140, it should be understood the needle slot 148 can be in a bottom of the needle shaft 140 or a side of the needle shaft 140, which needle-slot location can be on a same or different side of the RICC insertion assembly 100 as that of the coupler-housing slot 186, the slit 200 of the gasket 198, or both. The needle slot 148 can have a width sized in accordance with an outer diameter of the access guidewire 106, which allows the access guidewire 106 to pass from the proximal portion of the needle shaft 140 through the needle tip 146 when the introducer needle-withdrawing step of the method set forth below is performed.

While the needle shaft 140 can include the foregoing needle slot 148, it should be understood the introducer needle 104 includes a needle lumen 158; however, the needle lumen 158 results from the combination of the needle shaft 140 and the sheath 142 over the needle shaft 140. Indeed, the sheath 142 over the needle shaft 140 can seal the needle slot 148 thereunder forming the needle lumen 158 of the introducer needle 104 and enable the syringe 110 to aspirate blood in accordance with the blood-aspirating step of the method set forth below.

The sheath 142 can include a sheath tip 160 in a distal portion of the sheath 142 and a sheath opening 162 in a side of the proximal portion of the sheath 142.

The sheath tip 160 can include a relatively short taper from an outer diameter of the distal portion of the sheath 142 to an outer diameter of a distal end of the sheath 142, the latter of which can be commensurate with an outer diameter of the distal portion of the needle shaft 140. The taper can have a taper angle less than the primary-bevel angle of the primary bevel 154 of the needle tip 146, which, in turn, can be less than the tip-bevel angle of the tip bevel 152 of the needle tip 146. The sheath tip 160 including such a taper can be configured to provide a smooth transition from the needle tip 146 to the sheath body for the needle tract-establishing step of the method set forth below.

The sheath opening 162 can open to the needle slot 148 of the needle shaft 140 and form an opening in a side of the introducer needle 104 that allows the access guidewire 106 to pass into the introducer needle 104 through the sheath opening 162 and the needle slot 148 in the ready-to-deploy state of the RICC insertion assembly 100. Thus, the sheath opening 162 can have a width approximately commensurate with a width of the needle slot 148, which, in turn, can be sized in accordance with the diameter of the access guidewire 106. However, in some embodiments, the sheath opening 162 and the needle slot 148 can be wider than the diameter of the access guidewire 106 to accommodate the blade 192 of the valve module 180 to a side of the access guidewire 106 in the sheath opening 162. The sheath opening 162 can also have a length sufficient to allow the access guidewire 106 to pass through the sheath opening 162 and into the needle slot 148 while also accommodating the blade 192 of the valve module 180 under a distal end of the sheath opening 162. Notably, the sheath 142 over the needle shaft 140 can seal the needle slot 148 thereunder except for a portion of the needle slot 148 under the sheath opening 162. However, the valve module 180 or the gasket 198 thereof can seal over the needle slot 148 exposed by the sheath opening 162 by sealing the proximal portions of the needle shaft 140 and the sheath 142 therein, thereby enabling the syringe 110 to aspirate blood in accordance with the blood-aspirating step of the method set forth below.

The sheath 142, or a sheath body thereof, can be formed of a polymeric material configured to facilitate a smooth, consistent insertion of the introducer needle 104 from an area of skin to a blood-vessel lumen of a patient in accordance with the needle tract-establishing step of the method set forth below. In addition, the polymeric material can have mechanical properties at a thickness of the sheath 142 sufficient to prevent collapse of the sheath 142 into the needle slot 148 of the needle shaft 140 when the blood-aspirating step of the method set forth below is performed, notably, while also facilitating the cutting of the sheath 142 off the needle shaft 140 in accordance with the introducer needle-withdrawing step of the method set forth below. Such a polymeric material can include, but is not limited to, polyethylene, polypropylene, or polytetrafluoroethylene.

The needle hub 144 can include an access-guidewire groove 164 in a distal portion of the needle hub 144 and a needle-hub connector 166 in a proximal portion of the needle hub 144.

The access-guidewire groove 164 of the needle hub 144 can be configured to allow the access guidewire 106 to pass over the needle hub 144 and direct the access guidewire 106 into the access-guidewire channel 206 of the gasket 198, which, in turn, directs the access guidewire 106 into both the sheath opening 162 of the sheath 142 and the needle slot 148 of the needle shaft 140 thereunder. The access-guidewire groove 164 can be open such that the access guidewire 106 lies in the access-guidewire groove 164 in at least the ready-to-deploy state of the RICC insertion assembly 100. Advantageously, the open access-guidewire groove 164 can allow the access guidewire 106 to remain in place when the introducer needle 104 is withdrawn from the RICC insertion assembly 100 in accordance with the introducer needle-withdrawing step of the method set forth below.

The needle-hub connector 166 can include a needle-hub bore 168 and an optional needle-hub flange 170 about the needle-hub connector 166.

The needle-hub bore 168 of the needle-hub connector 166 can be configured to accept a syringe tip 172 of the syringe 110 therein for fluidly connecting the introducer needle 104 to the syringe 110. Indeed, the needle-hub bore 168 can have a Luer taper (e.g., a 6% taper) configured to accept the syringe tip 172 therein, which syringe tip 172 can be complementarily configured with a Luer taper.

The needle-hub flange 170 of the needle-hub connector 166 can be configured to screw together with internal threads 174 of a threaded collar 176 around the syringe tip 172 of the syringe 110. While the threaded collar 176 of the syringe 110 is optional, the needle-hub flange 170 can advantageously provide a so-called Luer lock-style connection with the internal threads 174 of the threaded collar 176 when both are present. This can provide added security against inadvertent disconnection of the introducer needle 104 and the syringe 110 over that provided by an otherwise Luer slip-style connection.

FIGS. 2-5 illustrate various view of the coupler 108 of the RICC insertion assembly 100 in accordance with some embodiments.

As shown, the coupler 108 can include a coupler housing 178 and a valve module 180 disposed in the coupler housing 178. However, it should be understood that the coupler housing 178 and the valve module 180 or the gasket 198 thereof can be molded together in an integral elastomeric or thermoplastic piece in some embodiments, the integral piece thereby including portions corresponding to the coupler housing 178 and the valve module 180 or the gasket 198 thereof. Whether the coupler 108 has the foregoing integral piece or separate pieces of the coupler housing 178 and valve module 180, the coupler 108 can also include a swivel arm 182 swivelably coupled to the coupler housing 178.

Figures 4, 5:
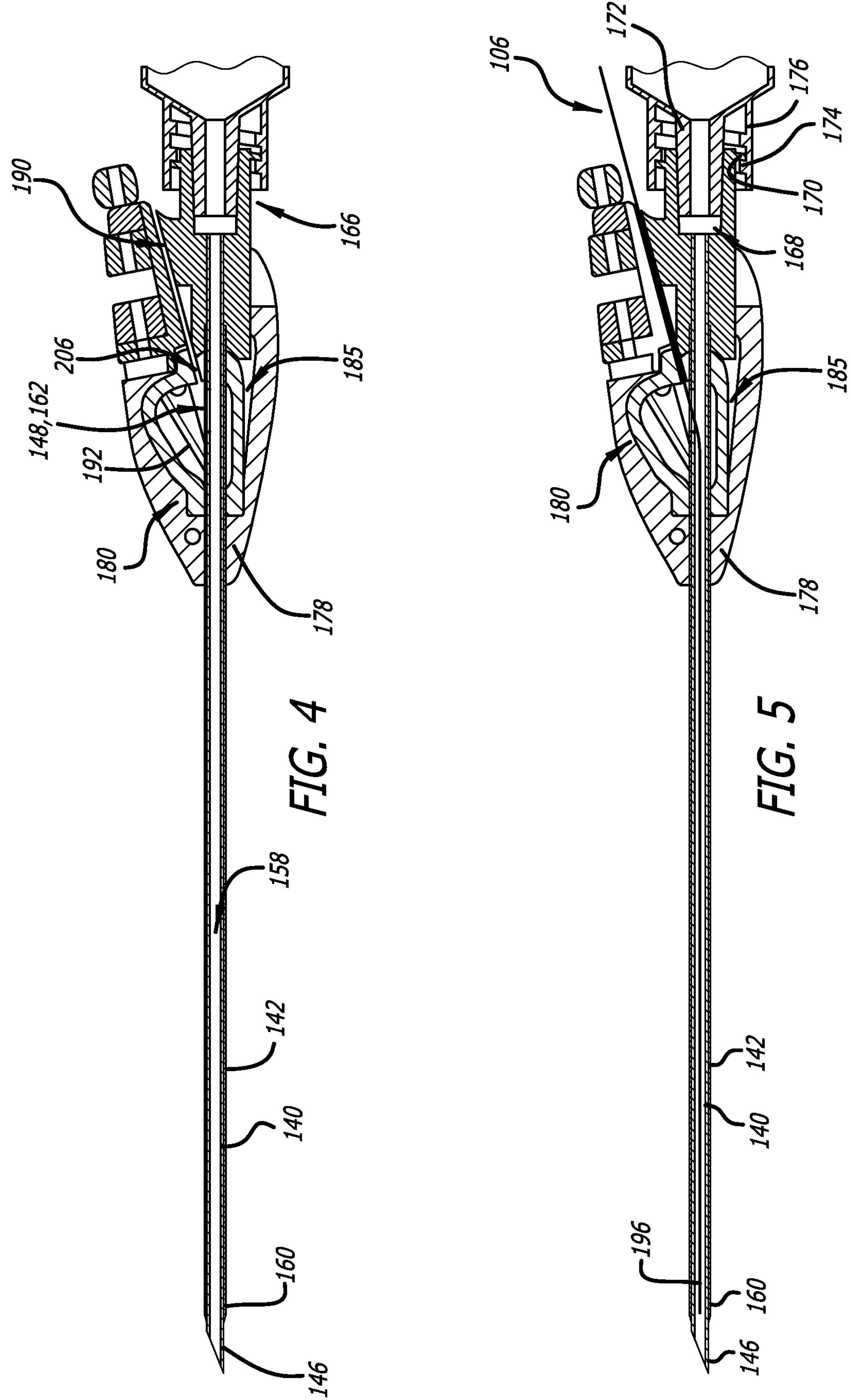
FIG. 4 illustrates a longitudinal cross section of a coupler and an introducer needle of the RICC insertion assembly with a gasket of a valve module of the coupler disposed in a valve-module compartment of a symmetric coupler housing of the coupler around the introducer needle in accordance with some embodiments.
FIG. 5 illustrates a longitudinal cross section of the coupler, the introducer needle, and an access guidewire of the RICC insertion assembly with the gasket of the valve module disposed in the valve-module compartment of the coupler housing around the introducer needle and the access guidewire in accordance with some embodiments.
Figure 13A:
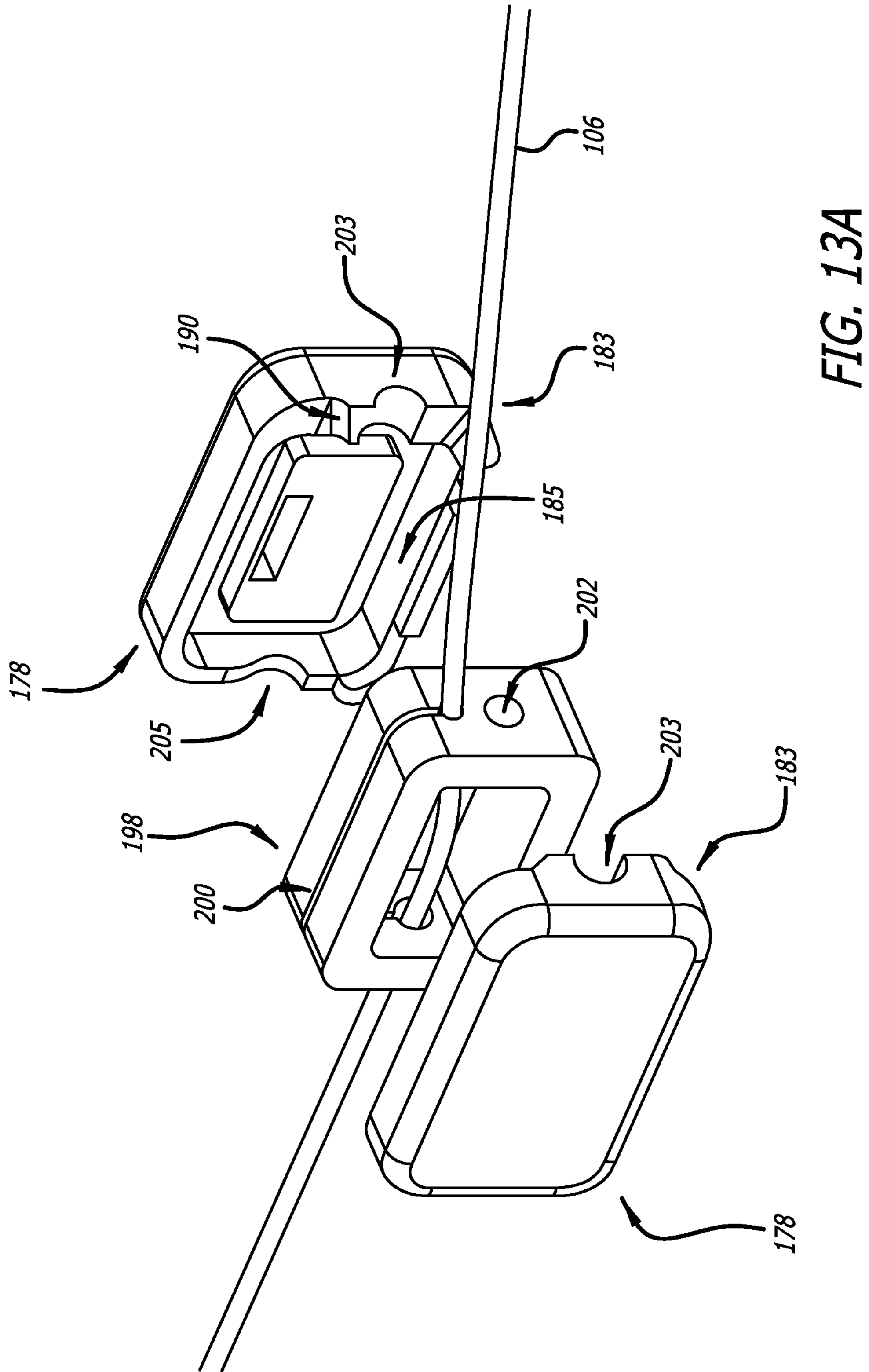
FIG. 13A illustrates an exploded view of the valve module including the gasket of FIG. 7 as well as the valve-module compartment of another symmetric coupler housing in accordance with some embodiments.

The coupler housing 178 can include a number of complementary molded pieces coupled together such as two molded pieces coupled together to form a body of the coupler housing 178. The body of the coupler housing 178 can be symmetric, for example, as shown in FIGS. 3 and 13A with two molded pieces or halves that are substantially mirror images of each other. Indeed, with respect to at least the coupler housing 178 of FIG. 13A, the two molded pieces or halves are substantially mirror images of each other in that they are mirror images but for their coupling features 183 for coupling with each other. Alternatively, the body of the coupler housing 178 can be asymmetric, for example, as shown in FIGS. 10-12, 13B, 13C, 14, 15, 16A and 16B with two molded pieces such as an open-box piece and a lid piece that are not related to each other by any symmetry operation. The body of the coupler housing 178 can also be in any shape of a number of hand-holdable shapes. In an example, the body of the coupler housing 178 can be ovoid as shown in FIG. 3, which body is configured to be comfortably held underhand (e.g., cradled) or overhand in either a left hand for a left-handed venipuncture or a right hand for a right-handed venipuncture with the RICC insertion assembly 100. In another example, the body of the coupler housing 178 can be more cuboid as shown in any figure of FIGS. 10-15, 16A, and 16B, which body is likewise configured to be comfortably held underhand or overhand for a venipuncture with the RICC insertion assembly 100. To further facilitate such venipunctures, an outside of each piece of the molded pieces can be textured as shown in FIG. 3 with grip-enhancing arcuate ridges 184 or the like. An inside of each piece of the molded pieces can include a depression that forms a valve-module compartment 185 and a needle-hub receptacle when the molded pieces are coupled together as shown. (See FIGS. 4 and 5, which include the valve module 180 or the gasket 198 thereof disposed in a depression of a molded piece [e.g., a molded half] that forms part of the valve-module compartment 185. FIGS. 4 and 5 also include the needle hub 144 of the introducer needle 104 disposed in a depression of the same molded piece that forms the needle-hub receptacle.) Opposite molded pieces of the coupler housing 178 such as the two molded pieces shown in FIG. 3 can include lock-button through holes for the pair of lock buttons 188 of the needle-hub lock. (See FIG. 3 for the pair of lock buttons 188 extending through the corresponding pair of lock-button through holes.)

Figure 13C:
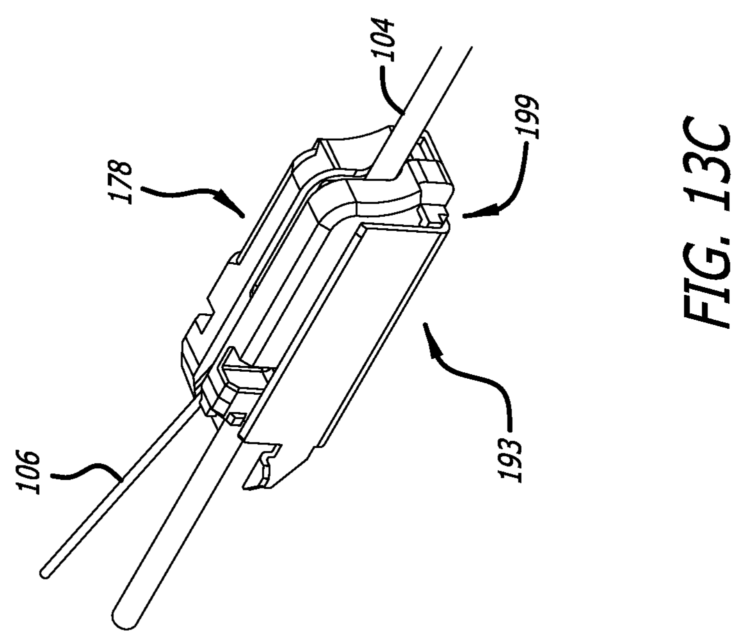
FIG. 13C illustrates an assembly of the valve module including the gasket of FIG. 7, the other asymmetric coupler housing of FIG. 13B, and the compression clip clipping the assembly together in accordance with some embodiments.
Figure 13B:
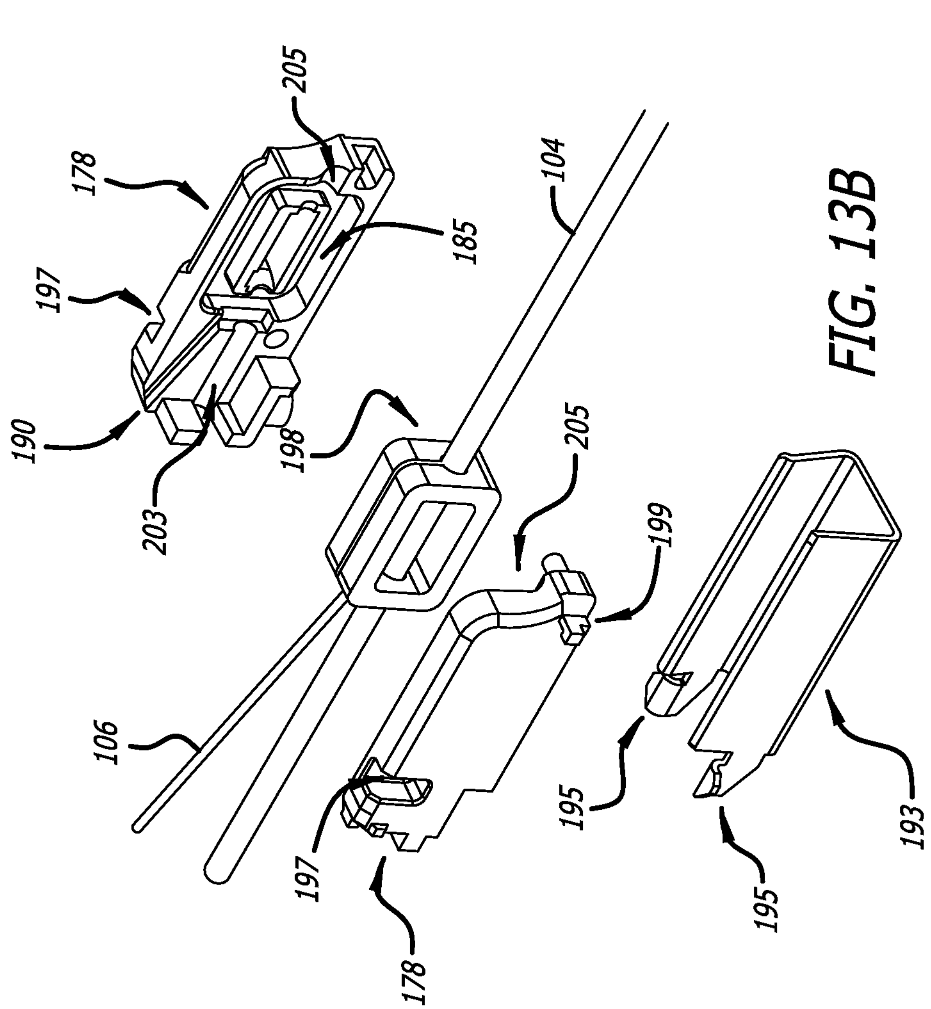
FIG. 13B illustrates an exploded view of the valve module including the gasket of FIG. 7 as well as the valve-module compartment of another asymmetric coupler housing together with a compression clip in accordance with some embodiments.
Figures 14, 15:
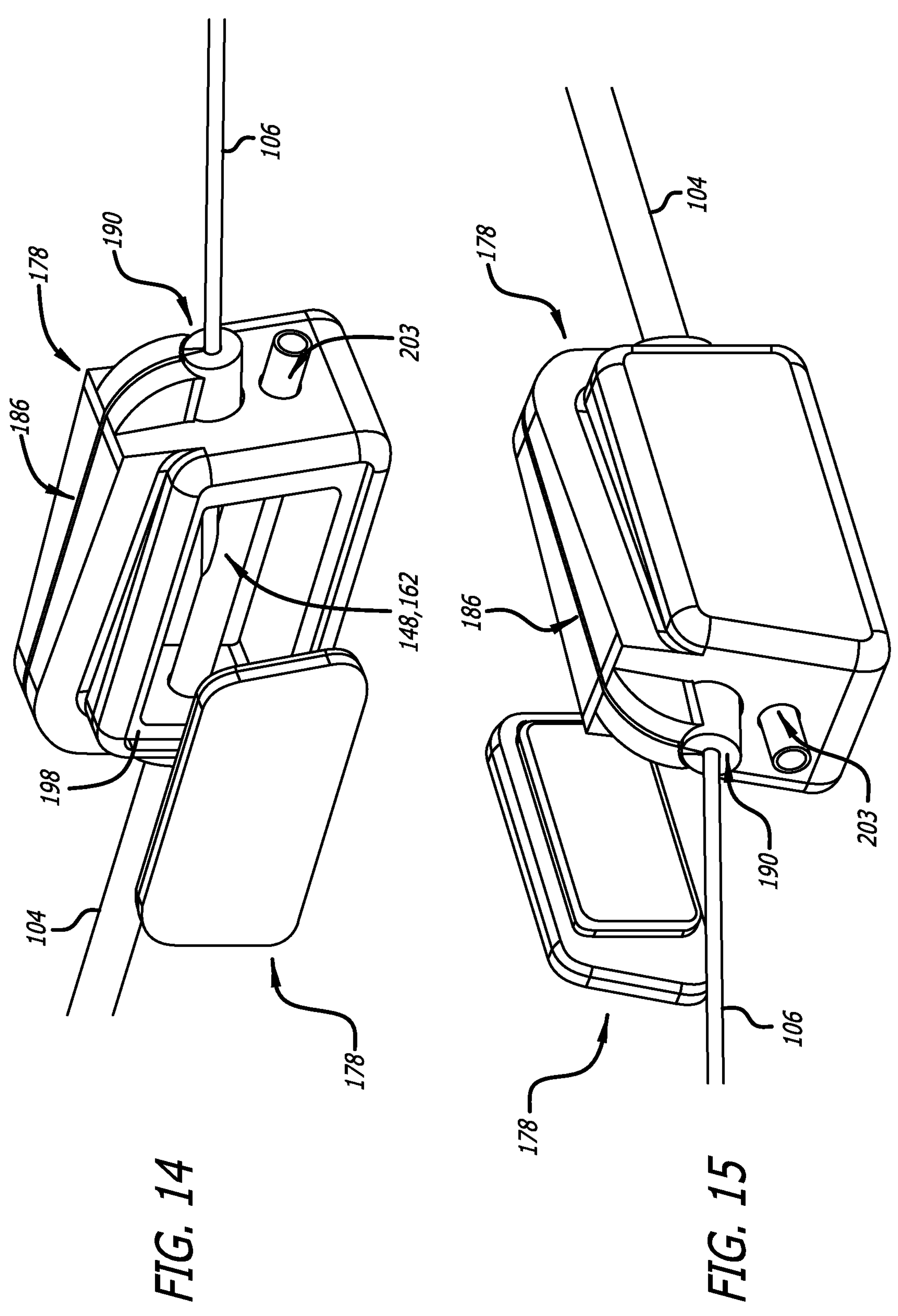
FIG. 14 illustrates an exploded view of the valve module including the gasket of FIG. 7 partially disposed in the valve-module compartment of another asymmetric coupler housing in accordance with some embodiments.
FIG. 15 illustrates another exploded view of the valve module including the gasket of FIG. 7 partially disposed in the valve-module compartment of the other asymmetric coupler housing in accordance with some embodiments.

In addition, the opposite molded pieces such as the two molded pieces shown in FIGS. 3, 13A, and 13B can form an access-guidewire conduit 190 of the coupler housing 178 therebetween. Otherwise, the access-guidewire conduit 190 can be formed in a single piece of the coupler housing 178 such as that shown in FIG. 10. The access-guidewire conduit 190 can be configured to direct the access guidewire 106 over the access-guidewire groove 164 of the needle hub 144, accept the access guidewire 106 from the access-guidewire groove 164 of the needle hub 144, or both. The access guidewire 106 can be subsequently directed by the access-guidewire conduit 190 or the access-guidewire groove 164 into the access-guidewire channel 206 through the proximal-end portion of the gasket 198, which access-guidewire channel 206, in turn, can direct the access guidewire 106 into both the sheath opening 162 of the sheath 142 and the needle slot 148 of the needle shaft 140 thereunder. Lastly, the coupler housing 178 can include a longitudinal coupler-housing slot 186 formed among the molded pieces such as between the two molded pieces shown in FIG. 3. The coupler-housing slot 186 can be configured to allow the access guidewire 106 to escape from the coupler housing 178 when the introducer needle 104 is withdrawn from the coupler 108 in the introducer needle-withdrawing step of the method set forth below. Notably, the coupler-housing slot 186 can be in a bottom of the coupler housing 178 as shown in FIG. 3, a top of the coupler housing 178, or a side of the coupler housing 178. In addition, the coupler-housing slot 186 can be located on the same or different side of the RICC insertion assembly 100 as that of needle slot 148, the slit 200 of the gasket 198, or both.

The valve-module compartment 185 can be configured to hold the valve module 180 or the gasket 198 thereof in the valve-module compartment 185. Indeed, the valve-module compartment 185 can include the valve module 180 or the gasket 198 thereof disposed in the valve-module compartment 185 in the ready-to-deploy state of the RICC insertion assembly 100. While the valve-module compartment 185 can be configured to compress the gasket 198 of the valve module 180, for example, by sides of the coupler housing 178 (e.g., the sides of the open-box piece and the lid piece shown between FIGS. 11 and 12 or FIGS. 14 and 15) in the ready-to-deploy state of the RICC insertion assembly 100, the valve-module compartment 185 can be further configured with sufficient space to allow any pieces or pieces of the gasket 198 set forth below to separate for the escape of the access guidewire 106 when compression is relieved, the introducer needle 104 is withdrawn from the coupler 108, or a combination thereof.

The needle-hub receptacle can be configured to hold the needle hub 144 of the introducer needle 104 therein. Indeed, the needle-hub receptacle can include the needle hub 144 inserted therein in the ready-to-deploy state of the RICC insertion assembly 100. Notably, a needle-hub lock configured to lock the needle hub 144 in the needle-hub receptacle can be positioned about the needle-hub receptacle. A pair of lock buttons 188 (e.g., spring-loaded lock buttons) of the needle-hub lock can be distributed between opposing sides of the coupler 108, particularly in the lock-button through holes of the two molded pieces of the coupler housing 178 shown in FIG. 3 such that each lock button of the pair of lock buttons 188 extends through the coupler housing 178 on its respective side of the coupler 108. The pair of lock buttons 188 can be configured to unlock the needle hub 144 when the pair of lock buttons 188 are pressed into the coupler 108 for withdrawal of the introducer needle 104 from the coupler 108 in the introducer needle-withdrawing step of the method set forth below.

The valve module 180 can include an elastomeric gasket 198 and, optionally, a blade 192. While the gasket 198 can range from a relatively low Shore A durometer to a relatively high Shore A or low Shore D durometer, it should be understood the gasket 198 can alternatively be a rigid thermoplastic insert or the like in some embodiments. Such an insert can be formed of a unitary piece or two or more complementary pieces mated together in any shape set forth below for the gasket 198, but the insert can be fitted with elastomeric components such as a relatively thin, compressible gasket between any two pieces of the insert, compressible 'O'-rings in the proximal needle through-hole 202, the distal needle through-hole 204, and the access-guidewire channel 206, or the like for creating a substantially air-tight space within the insert around the proximal portion of the introducer needle 104 and the distal portion of the access guidewire 106.

Figures 6, 7:
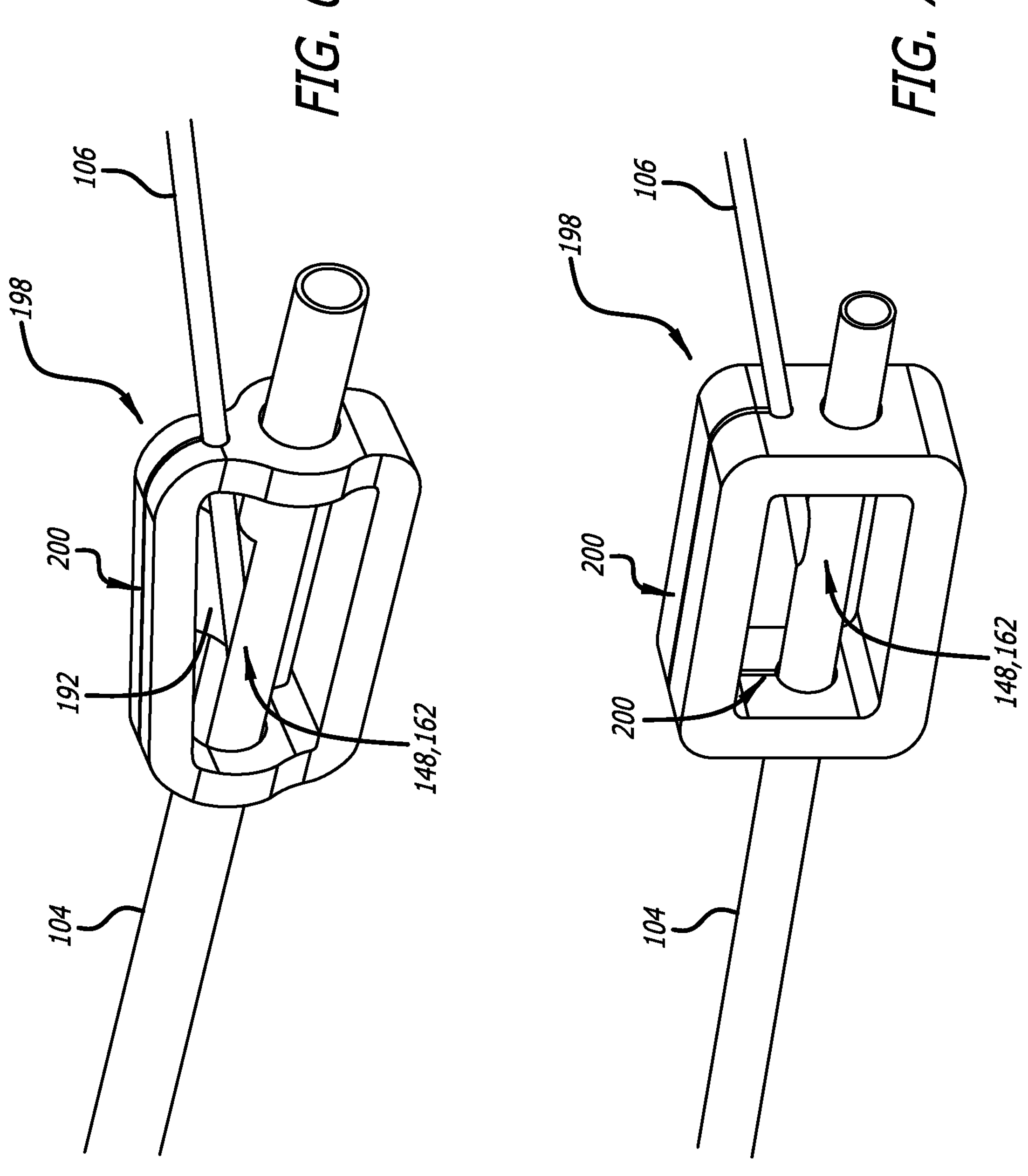
FIG. 6 illustrates a perspective view of another gasket of the valve module around the introducer needle and the access guidewire in accordance with some embodiments.
FIG. 7 illustrates a perspective view of yet another gasket of the valve module around the introducer needle and the access guidewire in accordance with some embodiments.

The gasket 198 can be configured to encircle at least a portion of the valve-module compartment 185 of the coupler housing 178 along a length of the valve-module compartment 185. Such a gasket can approximate a rectangle or a right trapezoid when viewed from a major side as respectively shown in FIGS. 6 and 7; however, it should be understood the gasket 198 is not limited to the foregoing shapes. The gasket 198 can be configured to be compressed in the valve-module compartment 185, for example, by sides of the coupler housing 178 (e.g., the sides of the open-box piece and the lid piece) as shown between FIGS. 11 and 12 or FIGS. 14 and 15, around a proximal portion of the introducer needle 104 in the ready-to-deploy state of the RICC insertion assembly 100, thereby creating, optionally, with a lubricant, a substantially air-tight space within the gasket 198 around the proximal portion of the introducer needle 104 for at least aspirating blood in accordance with the blood-aspirating step of the method set forth below. The gasket 198 can also be configured to be compressed in the valve-module compartment 185 around the distal portion of the access guidewire 106 in the ready-to-deploy state of the RICC insertion assembly 100, thereby further creating optionally, with the lubricant, the substantially air-tight space within the gasket 198 around the distal portion of the access guidewire 106 while allowing the access guidewire 106 to pass into the opening in the side of the introducer needle 104, specifically the sheath opening 162 of the sheath 142 and the needle slot 148 of the needle shaft 140. Notably, the compression of the gasket 198 in the valve-module compartment 185 is optimized to meet at least a minimum pressure requirement for the aspirating of blood with the introducer needle 104 while maintaining a lowest-possible access-guidewire insertion force for the access guidewire 106 when inserting the access guidewire 106 into the access-guidewire channel 206 of the gasket 198 and passing it into the opening in the side of the introducer needle 104.

The gasket 198 can be formed of a unitary piece or two or more complementary pieces mated together. When the gasket 198 is formed of the unitary piece, the gasket 198 can include a longitudinal slit 200 through a top or bottom portion of the gasket 198 configured to separate and allow the access guidewire 106 to escape from the gasket 198 when the compression on the gasket 198 is relieved, the introducer needle 104 is withdrawn from the coupler 108, or a combination thereof. Indeed, FIGS. 6, 7, 8A, 8B, 10, 13A and 13B show the slit 200 through the top portion of the gasket 198, which separates and allows the access guidewire 106 to escape from the top portion of the gasket 198 when the compression on the gasket 198 is relieved, the introducer needle 104 is withdrawn from the coupler 108, or both. When the gasket 198 is formed of the two-or-more complementary pieces, the gasket 198 can be substantially symmetric or asymmetric. For example, the gasket 198 can be substantially symmetric along a longitudinal plane of symmetry through a majority of the gasket 198 when the gasket 198 is formed of two complementary pieces that substantially are mirror images of each other. (See FIG. 9.) When the gasket 198 is asymmetric, however, the two-or-more complementary pieces of the gasket 198 are not related to each other by any symmetry operation. Notably, the gasket 198 need not include the slit 200 through the top or bottom portion of the gasket 198 when formed of the two-or-more complementary pieces because the two-or-more complementary pieces of the gasket 198 can be configured to separate and allow the access guidewire 106 to escape from the gasket 198 when compression on the gasket 198 is relieved, the introducer needle 104 is withdrawn from the coupler 108, or a combination thereof.

Whether the gasket 198 is formed of the unitary piece or the two-or-more complementary pieces, the gasket 198 can include a proximal needle through-hole 202 through a proximal-end portion of the gasket 198 and a distal needle through-hole 204 aligned with the proximal needle through-hole 202 through a distal-end portion of the gasket 198, wherein the proximal needle through-hole 202 and the distal needle through-hole 204 can be coincident with or offset from a central longitudinal axis of the gasket 198. Further, the gasket can include an access-guidewire channel 206 through the proximal-end portion of the gasket 198 proximate the proximal needle through-hole 202. The proximal needle through-hole 202 can be configured to align with a proximal needle through-hole 203 of the coupler housing 178, when present, the distal needle through-hole 204 can be configured to align with a distal needle through-hole 205 of the coupler housing 178, when present, and the access-guidewire channel 206 can be configured to align with the access-guidewire conduit 190, the access-guidewire groove 164, or both, when present. Notably, when the gasket 198 is formed of the two-or-more complementary pieces such as the two complementary pieces of the gasket 198 shown in FIG. 9, the proximal needle through-hole 202, the distal needle through-hole 204, and the access-guidewire channel 206 can be formed among the two-or-more pieces of the gasket 198 such as between the two pieces of the gasket 198 when the two-or-more pieces of the gasket 198 are mated together. For example, half of each through-hole or channel of the proximal needle through-hole 202, the distal needle through-hole 204, and the access-guidewire channel 206 can be formed in each of the foregoing two pieces of the gasket 198 to complete the proximal needle through-hole 202, the distal needle through-hole 204, and the access-guidewire channel 206 when the two pieces of the gasket 198 are mated together.

Figures 8A, 8B, 9:
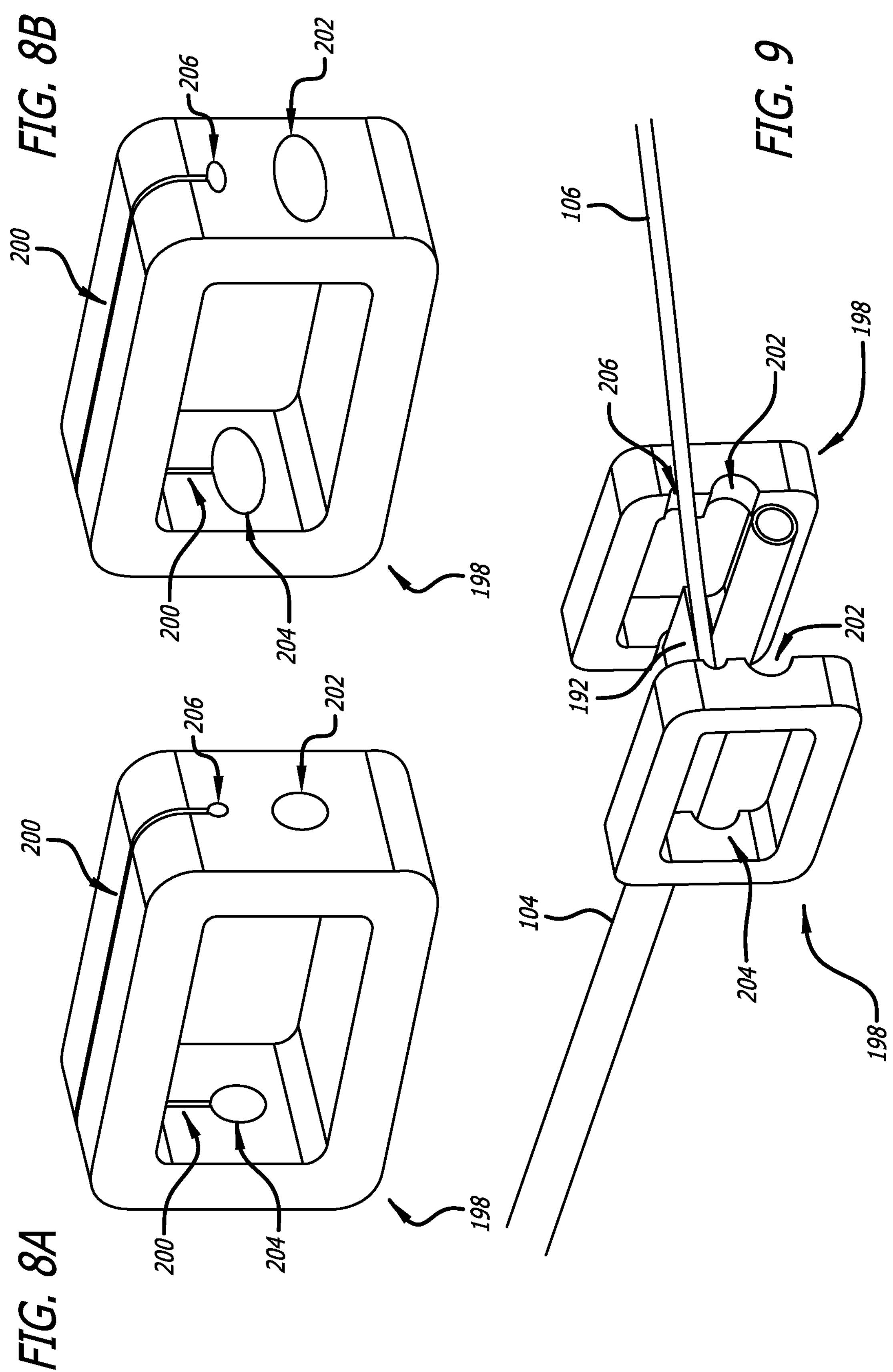
FIG. 8A illustrates a detailed view of the gasket of FIG. 7 in accordance with some embodiments.
FIG. 8B illustrates a detailed view of the gasket of FIG. 7 having a differently shaped proximal needle through-hole, distal needle through-hole, and access-guidewire channel in accordance with some embodiments.
FIG. 9 illustrates an exploded view of a multipiece alternative of the gasket of FIG. 7 in accordance with some embodiments.
Figure 10:
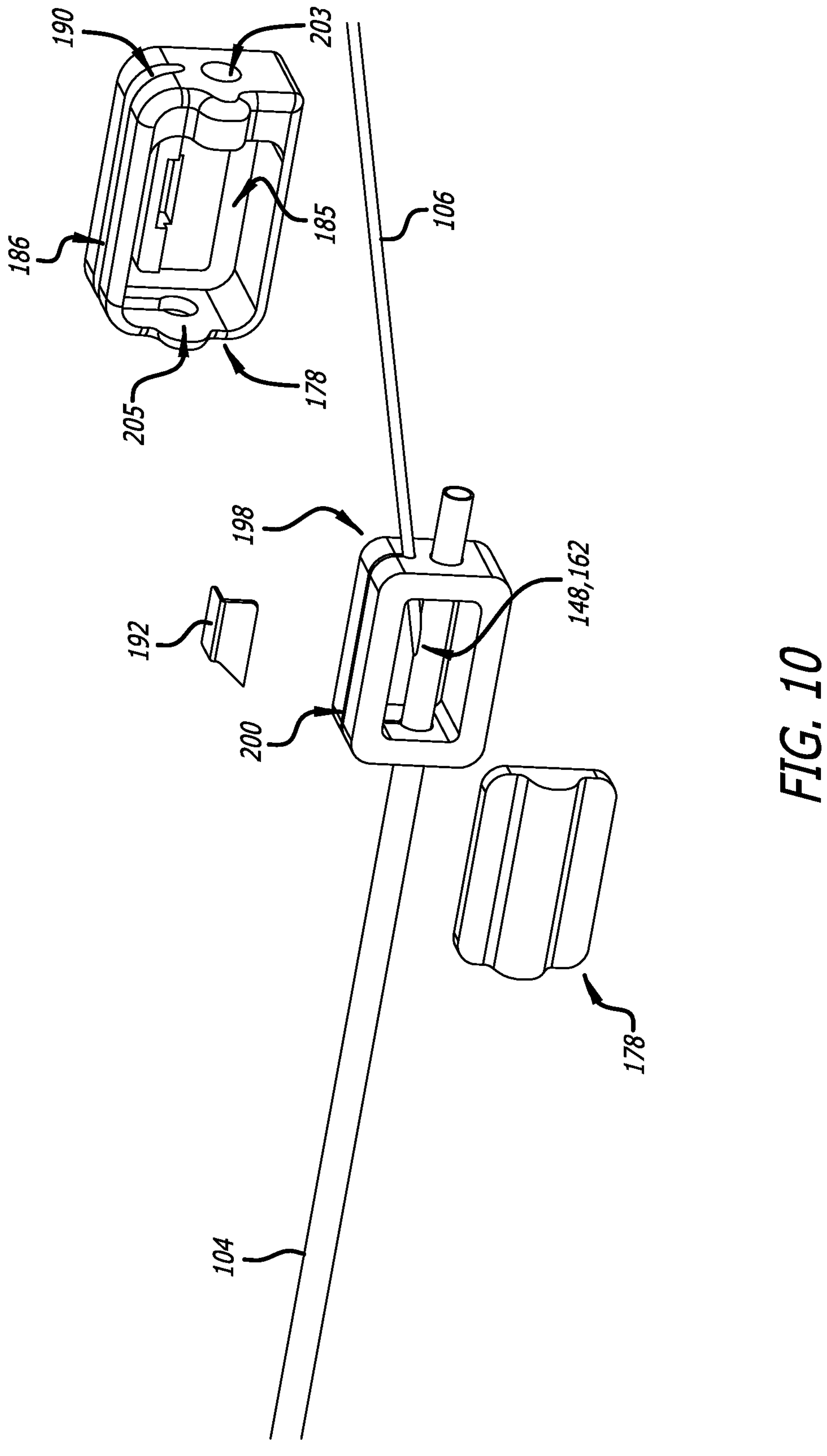
FIG. 10 illustrates an exploded view of the valve module including a blade and the gasket of FIG. 7 as well as the valve-module compartment of an asymmetric coupler housing in accordance with some embodiments.
Figure 11:
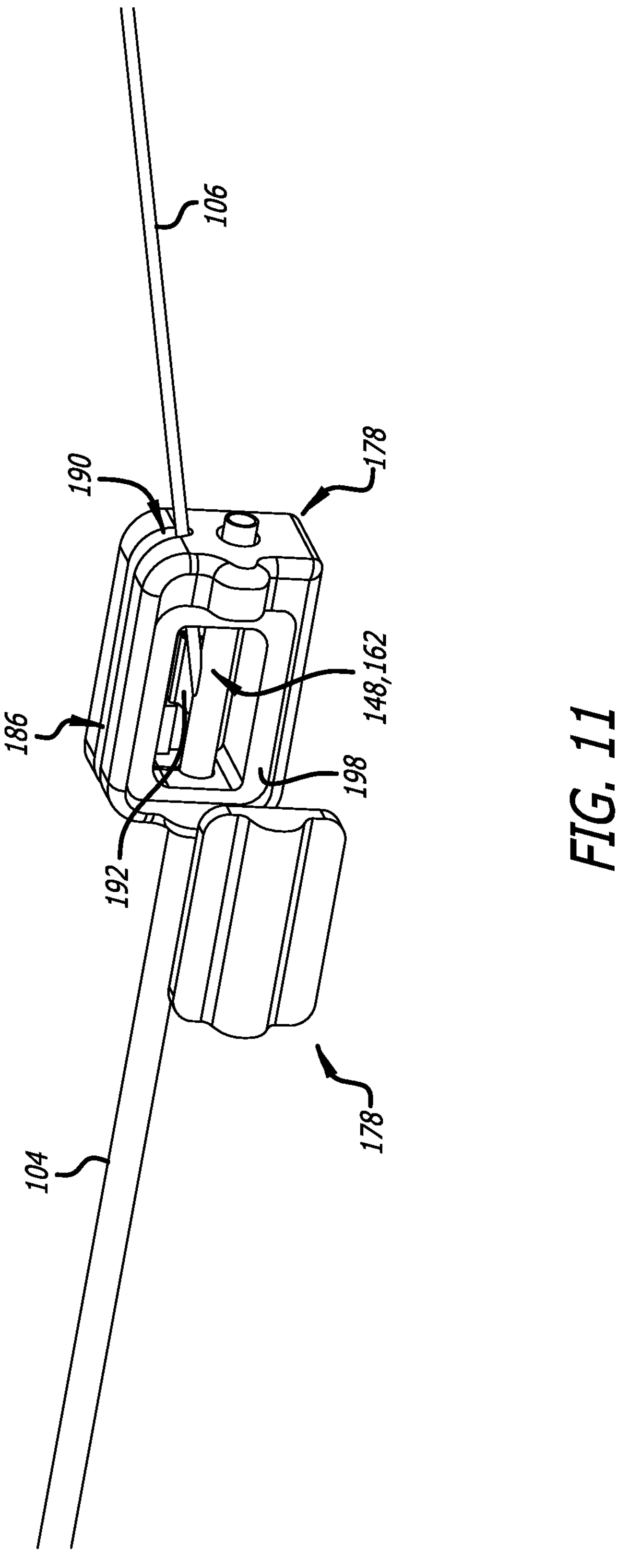
FIG. 11 illustrates the valve module of FIG. 10 partially disposed in the coupler housing thereof in accordance with some embodiments.
Figure 12:
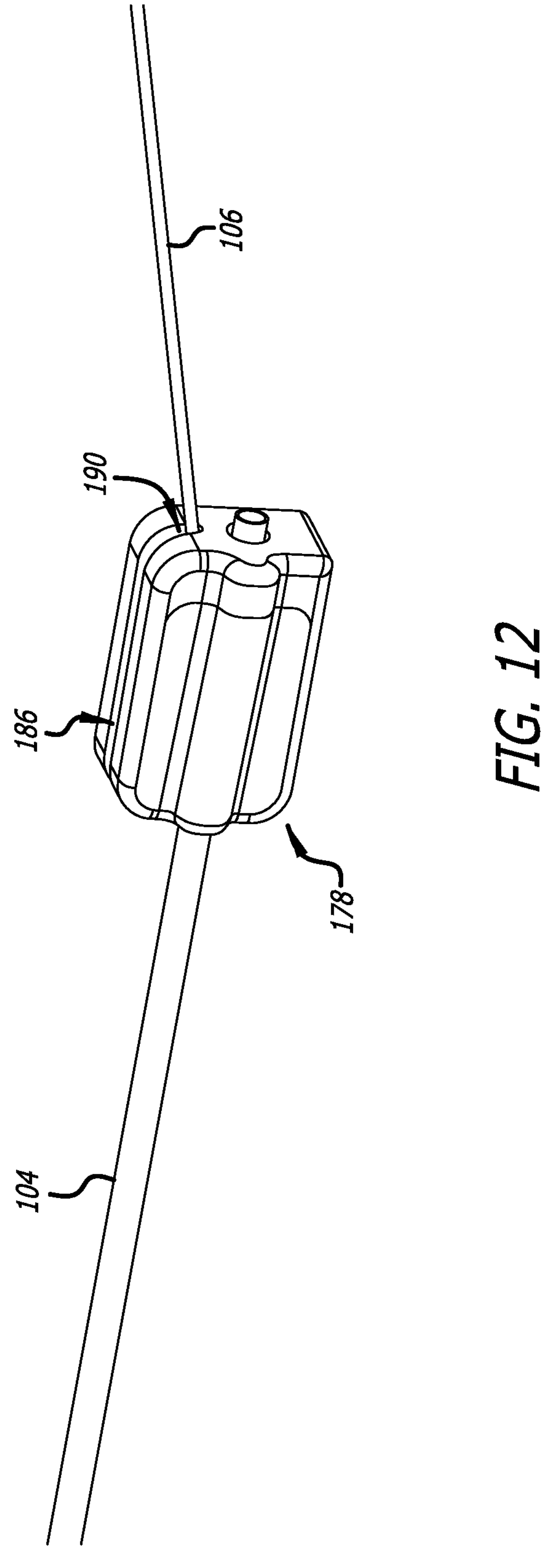
FIG. 12 illustrates the valve module of FIG. 10 completely disposed in the coupler housing thereof in accordance with some embodiments.

Each through-hole of the proximal needle through-hole 202 and the distal needle through-hole 204 can be circular in cross-section with an inner diameter commensurate with, larger than, or smaller than an outer diameter of the introducer needle 104. If any through-hole of the proximal needle through-hole 202 and the distal needle through-hole 204 is not circular in cross-section, the proximal needle through-hole 202 or the distal needle through-hole 204, as the case might be, can be oval in cross-section as shown in FIG. 8B, wherein a major axis of the proximal needle through-hole 202 or the distal needle through-hole 204 is commensurate with, larger than, or smaller than the outer diameter of the introducer needle 104, a minor axis of the proximal needle through-hole 202 or the distal needle through-hole 204 is commensurate with, larger than, or smaller than the outer diameter of the introducer needle 104, and the minor axis is smaller than the major axis. The proximal needle through-hole 202 and the distal needle through-hole 204 are, thereby, configured to accept therethrough the proximal portion of the introducer needle 104 such that the proximal portion of the introducer needle 104 passes through the proximal and distal needle through-holes 202 and 204 in the ready-to-deploy state of the RICC insertion assembly 100. Notably, when the gasket 198 is formed of the unitary piece, the distal needle through-hole 204 can be coincident with a distal terminal portion of the slit 200 through the top or bottom portion of the gasket 198, as the case might be; however, the inner diameter, major axis, or minor axis can, again, be commensurate with, larger than, or smaller than the outer diameter of the introducer needle 104.

The access-guidewire channel 206, which can be circular in cross-section with an inner diameter commensurate with, larger than, or smaller than the outer diameter of the access guidewire 106, can be through the proximal-end portion of the gasket 198, as set forth above. If the access-guidewire channel 206 is not circular in cross-section, the access-guidewire channel 206 can be oval in cross-section as shown in FIG. 8B, wherein a major axis of the access-guidewire channel 206 is commensurate with, larger than, or smaller than the outer diameter of the access guidewire 106, a minor axis of the access-guidewire channel 206 is commensurate with, larger than, or smaller than the outer diameter of the access guidewire 106, and the minor axis is smaller than the major axis. The access-guidewire channel 206 can form an acute angle with the proximal needle through-hole 202, thereby directing the distal portion of the access guidewire 106 into the proximal portion of the introducer needle 104 through both the sheath opening 162 of the sheath 142 and the needle slot 148 of the needle shaft 140. Notably, when the gasket 198 is formed of the unitary piece, the access-guidewire channel 206 can be coincident with a proximal terminal portion of the slit 200 through the top or bottom portion of the gasket 198 as the case might be; however, the inner diameter, major axis, or minor axis of the access-guidewire channel 206 can, again, be commensurate with, larger than, or smaller than the outer diameter of the access guidewire 106, though it need not be any different than the slit 200 itself. That is, the access-guidewire channel 206 can be the proximal terminal portion of the slit 200.

Figures 16A, 16B:
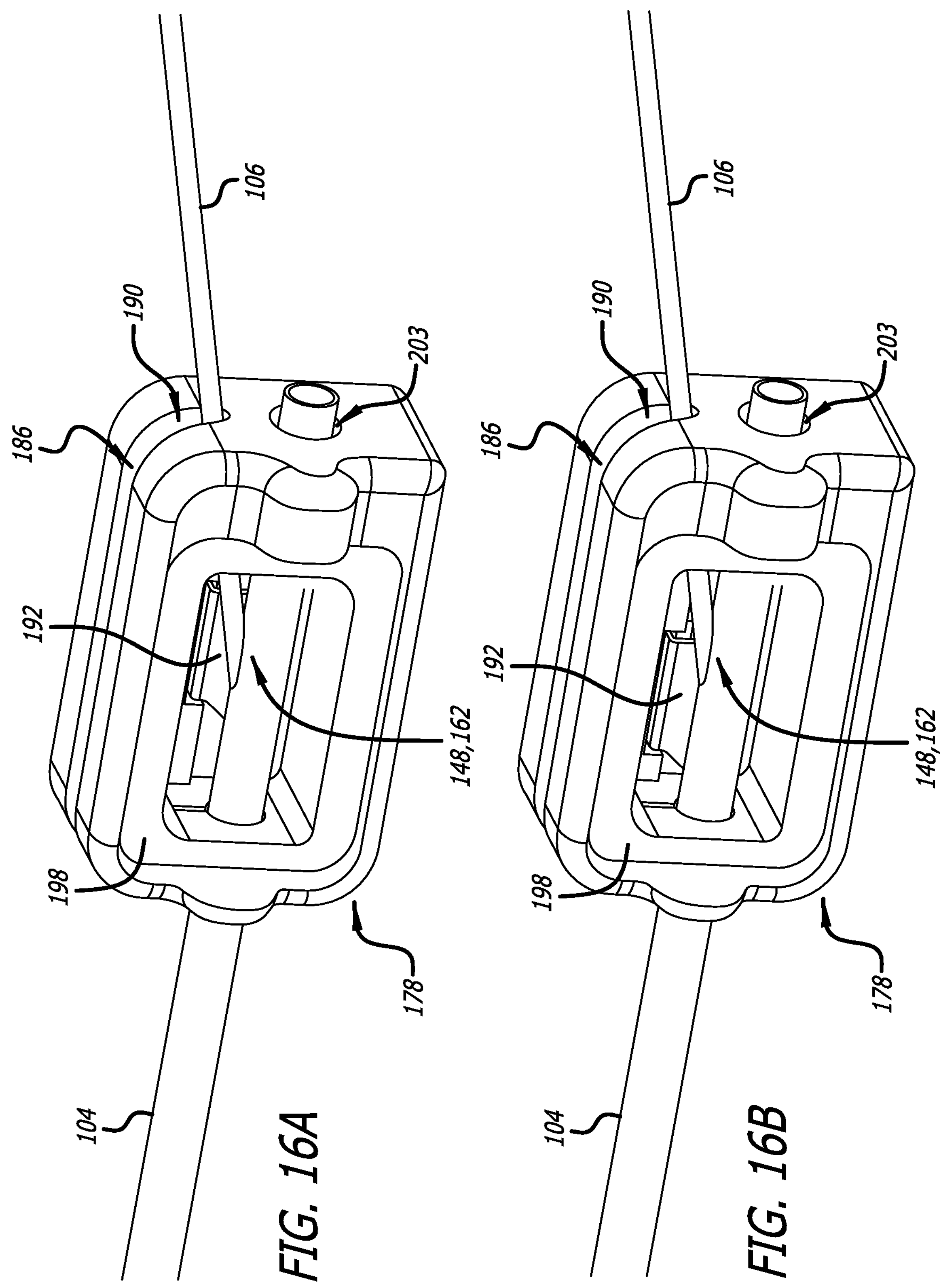
FIG. 16A illustrates a detailed view of the valve module disposed in the valve-module compartment of the asymmetric coupler housing of FIG. 11 with the blade to a side of the access guidewire in accordance with some embodiments.
FIG. 16B illustrates a detailed view of the valve module disposed in the valve-module compartment of the asymmetric coupler housing of FIG. 11 with the blade distal of the access guidewire in accordance with some embodiments.

The blade 192 can extend into the valve module 180 by way of the slit 200 or between two of the two-or-more pieces of the gasket 198 from an attachment point of the coupler housing 178 to which the blade 192 is coupled. Alternatively, the blade 192 can be incorporated into the gasket 198, itself, such that the blade 192 extends from the top portion of the gasket 198, for example. Whether the blade 192 extends into the valve module 180 through the gasket 198 or from the top portion of the gasket 198, itself, the blade 192 can extend into the needle slot 148 of the needle shaft 140 such that the blade 192 is disposed in the needle slot 148 distal of the access guidewire 106 under the distal end of the sheath opening 162 of the sheath 142 as shown in FIG. 16B or to a side of the access guidewire 106 as shown in FIG. 16A. The blade 192 can include a distal facing blade edge configured to cut the sheath 142 off the needle shaft 140 as the introducer needle 104 is withdrawn in a proximal direction from the coupler 108 in the introducer needle-withdrawing step of the method set forth below. Cutting the sheath 142 off the needle shaft 140 allows the access guidewire 106 to escape from the needle shaft 140 by way of the needle slot 148. Notwithstanding the foregoing, it should be understood the guidewire, itself, can alternatively cut the sheath 142 off the needle shaft 140 as the introducer needle 104 is withdrawn in the proximal direction from the coupler 108, particularly in embodiments lacking the blade 192.

FIGS. 13B and 13C illustrate at least a portion of the coupler housing 178 including the gasket 198 of the valve module 180 disposed in the valve-module compartment 185 of the coupler housing 178 together with a compression clip 193 in accordance with some embodiments.

As shown, the coupler 108 can further include the compression clip 193 in addition to the coupler housing 178 and the valve module 180. When present, the compression clip 193 can be configured to fit over and clip together the opposite molded pieces of the coupler housing 178 with the gasket 198 of the valve module 180 disposed in the valve-module compartment 185 of the coupler housing 178, thereby compressing the gasket 198 under a spring-like load applied by the compression clip 193. Compressing the gasket 198 under such a load seals both the introducer needle 104 and the access guidewire 106 in the valve module 180 or the gasket 198 thereof, for example, in the ready-to-deploy state of the RICC insertion assembly 100. Notably, the compression clip 193 can be advantageous in reducing or eliminating the impact of any manufacturing variations across the coupler housing 178, the valve module 180, or both the coupler housing 178 and the valve module 180, thereby reducing or eliminating sealing-related challenges due to such manufacturing variations.

The compression clip 193 can vary in form and with respect to various additional features if any additional features are present. For example, the compression clip 193 can further include secondary clips 195 in a portion of the compression clip 193 such as a proximal-end portion thereof, wherein the secondary clips 195 are biased toward each other. When such secondary clips 195 are present in the compression clip 193, the opposite molded pieces of the coupler housing 178 can include complementary recesses 197 in outward-facing walls of a portion of the coupler housing 178 such as a proximal-end portion thereof, wherein the recesses 197 are configured to accept the biased secondary clips 195 therein. When the secondary clips 195 of the compression clip 193 are disposed in the recesses 197 of the coupler housing 178, the compression clip 193 and the coupler housing 178, together, prevent proximal or distal movement of the compression clip 193 and the coupler housing 178 relative to each other. Alternatively, the secondary clips 195 of the compression clip 193 can extend from an end portion of the compression clip 193 as shown but beyond end portions of the walls of the coupler housing 178 when the compression clip 193 fits over and clips together the opposite molded pieces of the coupler housing 178. In such a configuration, the secondary clips 195 can prevent movement of the compression clip 193 and the coupler housing 178 relative to each other in at least one direction. For example, if the secondary clips 195 of the compression clip 193 extend from the proximal-end portion of the compression clip 193 as shown but beyond the end portions of the walls of the coupler housing 178 in the proximal-end portion of the coupler housing 178, the secondary clips 195 can prevent movement of the compression clip 193 in a distal direction over the coupler housing 178, which is the direction opposite a location of the secondary clips 195 on the compression clip 193. To prevent movement of the compression clip 193 and the coupler housing 178 relative to each other in both directions, an opposite end portion of the compression clip 193 (e.g., a distal-end portion of the compression clip 193) can also include the secondary clips 195 extending therefrom beyond opposite end portions of the walls of the coupler housing 178 (e.g., the end portions of the walls of the coupler housing 178 in the distal-end portion of the coupler housing 178) when the compression clip 193 fits over and clips together the opposite molded pieces of the coupler housing 178. That said, one or more protrusions such as protrusion 199 shown in FIGS. 13B and 13C extending from an end portion of a wall of the coupler housing 178 beyond the end portion of the compression clip 193 can be employed like the secondary clips 195 to prevent movement of the compression clip 193 and the coupler housing 178 relative to each other. Indeed, any combination of one or more clips of the secondary clips 195 and the foregoing one-or-more protrusion can be employed to prevent movement of the compression clip 193 and the coupler housing 178 relative to each other.

Figure 17:
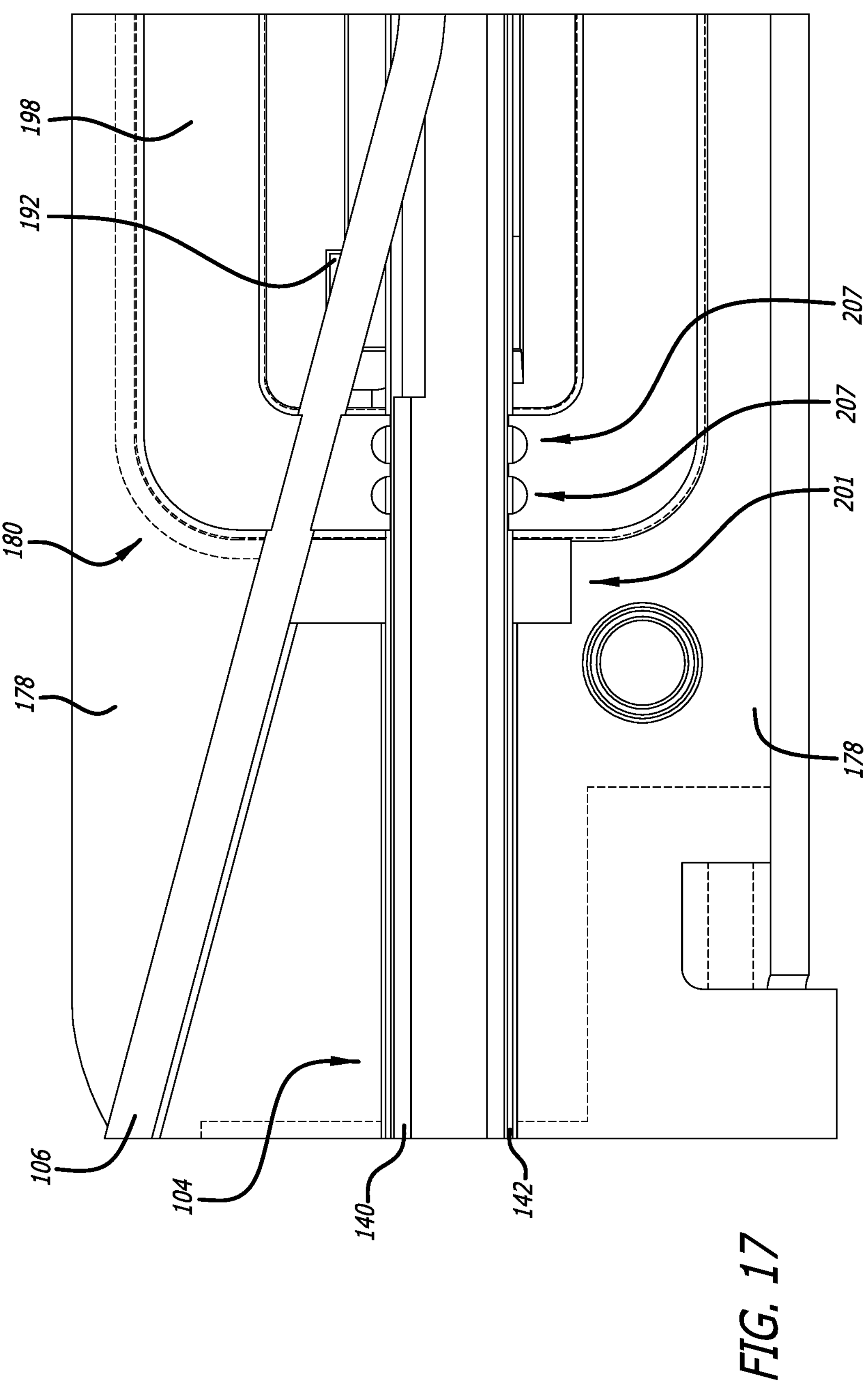
FIG. 17 illustrates a lubrication mechanism for lubricating the introducer needle and the access guidewire in accordance with some embodiments.
Figures 18, 19, 20:
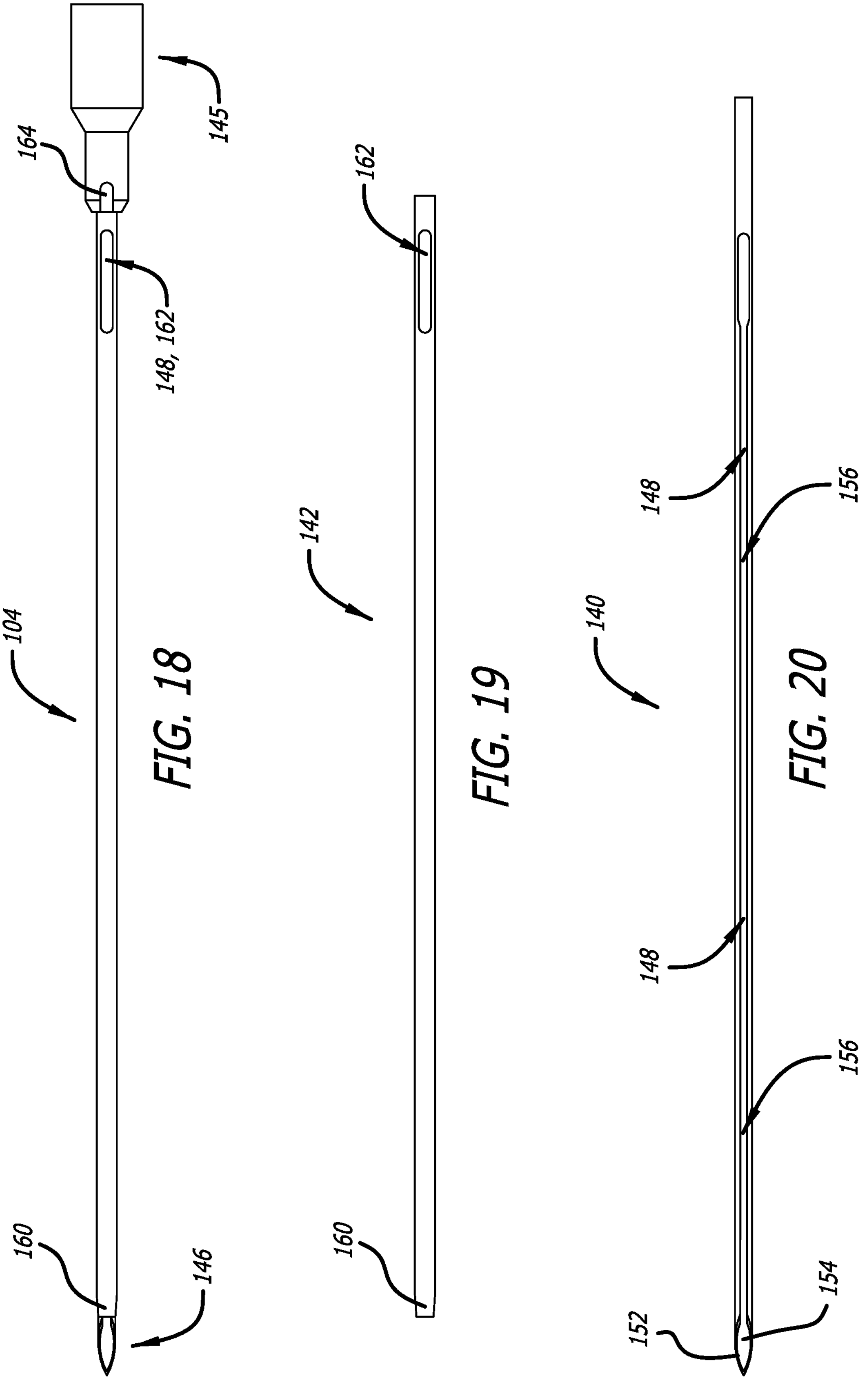
FIG. 18 illustrates a top view of the introducer needle in accordance with some embodiments.
FIG. 19 illustrates a sheath of the introducer needle in accordance with some embodiments.
FIG. 20 illustrates a needle shaft of the introducer needle in accordance with some embodiments.

FIG. 17 illustrates a lubrication mechanism for lubricating the introducer needle 104 and the access guidewire 106 in accordance with some embodiments.

While the lubrication mechanism for lubricating the introducer needle 104 and the access guidewire 106 can include applying lubricant to the introducer needle 104 and the access guidewire 106 prior to assembling the RICC insertion assembly 100, the lubrication mechanism can alternatively or additionally include one or more lubricant wells 201, one or more lubricant receptors 207, or a combination thereof distributed about the coupler housing 178, the gasket 198, or both the coupler housing 178 and the gasket 198.

A lubricant well 201 of the one-or-more lubricant wells 201 can be a compartment or chamber in the coupler housing 178 or the gasket 198 at least partially filled with the lubricant prior to inserting the introducer needle 104 or the access guidewire 106 into the coupler 108 during assembly of the RICC insertion assembly 100. A lubricant receptor 207 of the one-or-more lubricant receptors 207 can be a recess in the coupler housing 178 or the gasket 198, optionally, smaller than the compartment or chamber corresponding to the foregoing lubricant well 201, notably, without any of the lubricant therein prior to inserting the introducer needle 104 or the access guidewire 106 into the coupler 108 during assembly of the RICC insertion assembly 100. Indeed, such a lubricant receptor 207 can be configured to receive the lubricant from either the introducer needle 104 or the access guidewire 106, whether the introducer needle 104 or the access guidewire 106 is lubricated with the lubricant prior to being inserted into the coupler 108 or while the introducer needle 104 or the access guidewire 106 is inserted into the coupler 108 and passes through the one-or-more lubricant wells 201 during assembly of the RICC insertion assembly 100. And, upon such a lubricant receptor 207 receiving the lubricant in accordance with the foregoing, the lubricant receptor 207 can redistribute the lubricant over the introducer needle 104 or the access guidewire 106 as the introducer needle 104 or the access guidewire 106 is further inserted into the coupler 108 or withdrawn therefrom.

The one-or-more lubricant wells 201 and the one-or-more lubricant receptors 207 are not limited in their number, shape, size, or location in the coupler 108. In an example, the lubricant well 201 shown in FIG. 17 approximates, in shape, an eccentric annular compartment in the coupler housing 178 that, when at least partially filled with the lubricant, interfaces with both the introducer needle 104 and the access guidewire 106 due to its size, albeit partially with respect to the access guidewire 106; however, the lubricant well 201 shown in FIG. 17 could instead approximate two concentric annular compartments stacked such that they are respectively around the introducer needle 104 and the access guidewire 106, optionally, fluidly coupled at their edges to facilitate filling the annular compartments with the lubricant. Further, the lubricant well 201 shown in FIG. 17 can alternatively be located in a distal portion of the coupler housing 178 instead of a proximal portion of the coupler housing 178 as shown. In another example, the lubricant receptors 207 shown in FIG. 17 approximate, in shape, two linearly separated concentric annular recesses in the gasket 198 that interface with the introducer needle 104 only; however, two additional lubricant receptors 207 like those show in FIG. 17 can be added to the gasket 198 to interface with the access guidewire 106 as well. Further, the lubricant receptors 207 shown in FIG. 17 could instead approximate a single concentric annular recess around the introducer needle 104. Even further, the lubricant receptor 207 shown in FIG. 17 can alternatively be located in a distal portion of the gasket 198 instead of a proximal portion of the gasket 198 as shown.

The swivel arm 182 can include a swivel-arm connector 194 connected to an extension-leg connector of the one-or-more extension-leg connectors 118 in the ready-to-deploy state of the RICC insertion assembly 100. While not shown, the swivel-arm connector 194 can include an access-guidewire attachment point within the swivel-arm connector 194 to which the proximal end of the access guidewire 106 is attached in the ready-to-deploy state of the RICC insertion assembly 100. In combination with the distal end of the access guidewire 106 being disposed in the needle lumen 158 of the introducer needle 104, the loop in the access guidewire 106 set forth above can be enforced. Advantageously, the swivel arm 182 can be configured to flip the loop—or at least the one-or-more extension legs 116 of the RICC 102 thereof—between a sinistral side of the RICC insertion assembly 100 and a dextral side of the RICC insertion assembly 100 to accommodate both left-handed and right-handed venipunctures with the RICC insertion assembly 100. Indeed, the swivel arm 182 can be configured to flip the loop from the sinistral side of the RICC insertion assembly 100 as shown in FIG. 1 to the dextral side of the RICC insertion assembly 100 to accommodate a left-handed venipuncture with the RICC insertion assembly 100. Likewise, the swivel arm 182 can be configured to flip the loop from the dextral side of the RICC insertion assembly 100 to the sinistral side of the RICC insertion assembly 100 to accommodate a right-handed venipuncture with the RICC insertion assembly 100.

FIGS. 1, 2, and 5 illustrate various view of the access guidewire 106 of the RICC insertion assembly 100 in accordance with some embodiments.

The access guidewire 106 can include a proximal portion including a proximal end and a distal portion including a distal end. In the ready-to-deploy state of the RICC insertion assembly 100, the proximal end of the access guidewire 106 can be coupled to the swivel arm 182, particularly the access-guidewire attachment point within the swivel-arm connector 194 of the swivel arm 182. In addition, the proximal portion of the access guidewire 106 can extend along the primary lumen 128 of the RICC 102. The distal portion of the access guidewire 106 can also extend along the primary lumen 128 of the RICC 102, but the distal portion of the access guidewire 106 can further extend out the distal end of the RICC 102, into the valve module 180 or the gasket 198 thereof over the needle hub 144 by way of the access-guidewire groove 164, into the needle shaft 140 through both the sheath opening 162 of the sheath 142 and the needle slot 148 of the needle shaft 140, and along the needle lumen 158 of the introducer needle 104 in the ready-to-deploy state of the RICC insertion assembly 100. As shown in FIG. 5, the distal end of the access guidewire 106 can be disposed in the needle lumen 158 just proximal of the needle tip 146 in the ready-to-deploy state of the RICC insertion assembly 100. Again, the proximal and distal ends of the access guidewire 106 can enforce the loop in the access guidewire 106 in the ready-to-deploy state of the RICC insertion assembly 100, which loop the RICC 102 can be disposed over, thereby keeping the RICC insertion assembly 100 in a relatively compact form.

The access guidewire 106 can include a guidewire tip 196 in the distal portion of the access guidewire 106, which adopts a 'J' shape configured to prevent puncturing a back wall of a blood vessel. Such a guidewire tip can assume a straightened state in the ready-to-deploy state of the RICC insertion assembly 100 and a curved state when the guidewire tip 196 is advanced beyond the needle tip 146 (e.g., advanced into a blood-vessel lumen) in a deployed state of the RICC insertion assembly 100.

The access guidewire 106 can further include a bare-wire portion and a wound-wire portion distal of the bare-wire portion, proximal of the bare-wire portion, or both. While not shown, the bare-wire portion, when present, can distally extend through the access-guidewire channel 206 of the gasket 198 in at least the ready-to-deploy state of the RICC insertion assembly 100 such that the gasket 198 forms a fluid-tight seal around the bare-wire portion of the access guidewire 106. Notably, the foregoing bare-wire portion can instead be a flat-wound or ground-wound portion of the access guidewire 106, wherein the flat-wound portion includes windings of a tape instead of a round wire, and wherein the ground-wound portion includes windings of a round wire ground down to flatten the windings.

Introducer Assemblies

Figure 26:
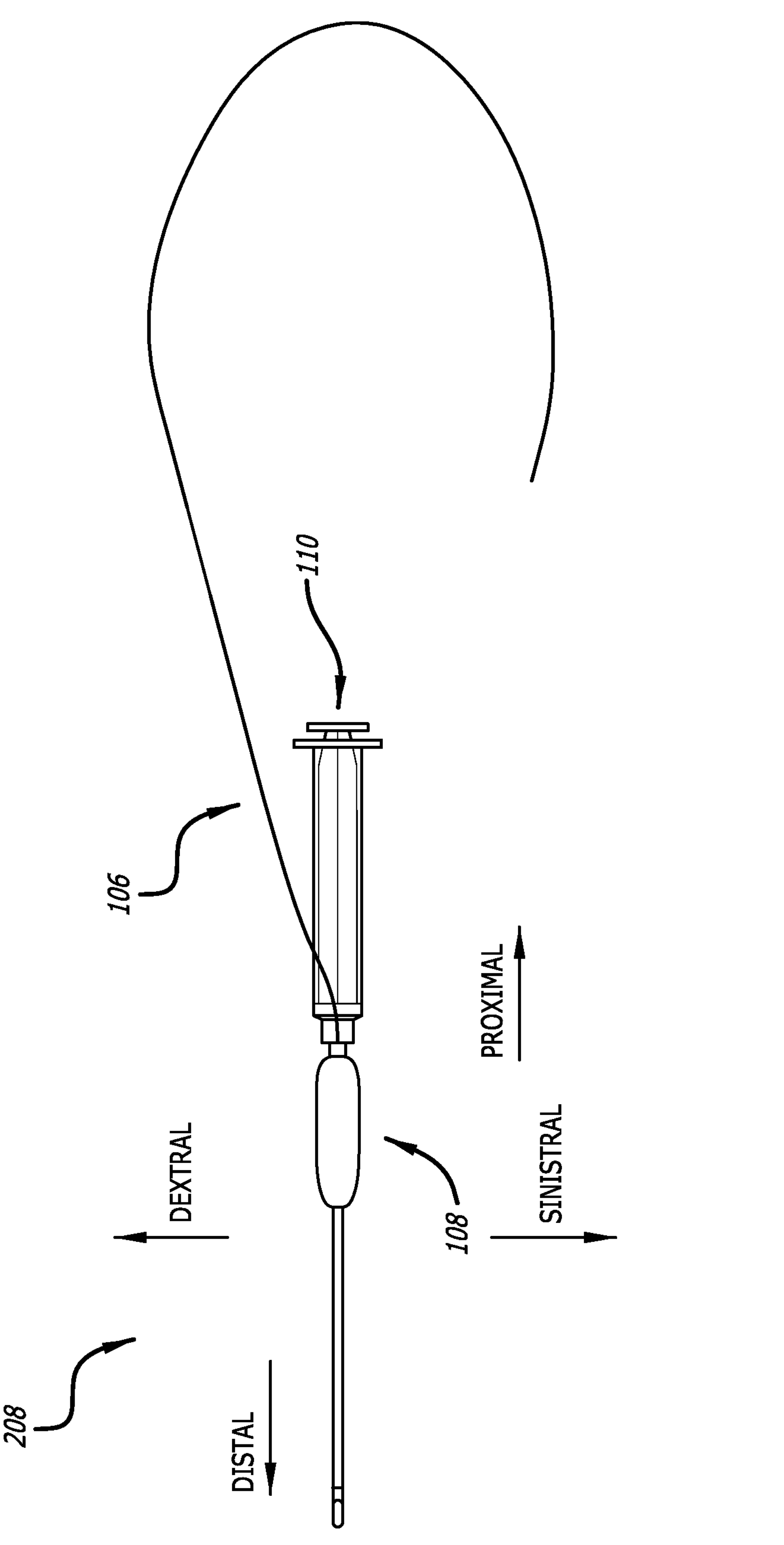
FIG. 26 illustrates a top view of an introducer assembly in accordance with some embodiments.

FIG. 26 illustrates a top view of an introducer assembly 208 in accordance with some embodiments.

As shown, the introducer assembly 208 can include the introducer needle 104, the coupler 108, the access guidewire 106, and, optionally, the syringe 110 fluidly coupled to the introducer needle 104 in a ready-to-deploy state of the introducer assembly 208. As set forth above, the introducer needle 104 can include the needle shaft 140 and the sheath 142 over the needle shaft 140. The needle shaft 140 can include the needle slot 148 extending from the proximal portion of the needle shaft 140 through the distal needle tip 146. The sheath 142 over the needle shaft 140 can seal the needle slot 148 thereunder except for the portion of the needle slot 148 under the sheath opening 162 in the proximal portion of the sheath 142. The coupler 108 can include the coupler housing 178 and the valve module 180 disposed in the valve-module compartment 185 of the coupler housing 178. The valve module 180 can include the gasket 198 encircling at least a portion of the valve-module compartment 185 of the coupler housing 178 along the length of the valve-module compartment 185. The gasket 198 in the valve-module compartment 185 can be compressed around the proximal portion of the introducer needle 104 in the ready-to-deploy state of the introducer assembly 208, thereby creating a substantially air-tight space within the gasket 198 around the proximal portion of the introducer needle 104. The access guidewire 106 can include the distal portion passing into the introducer needle 104 through both the sheath opening 162 of the sheath 142 and the needle slot 148 of the needle shaft 140. The gasket 198 in the valve-module compartment 185 can also be compressed around the distal portion of the access guidewire 106 in the ready-to-deploy state of the introducer assembly 208, thereby further creating the substantially air-tight space within the gasket 198 around the distal portion of the access guidewire 106. The access guidewire 106 can also include the distal end disposed in the introducer needle 104 just proximal of the needle tip 146 in the distal end of the introducer needle 104. Further details for the introducer needle 104, the coupler 108, the access guidewire 106, and the syringe 110 are set forth above in the context of the RICC insertion assembly 100.

Methods

Methods of the RICC insertion assembly 100 can include a method for inserting or placing the RICC 102 in a blood-vessel lumen of a patient. Such a method can include one or more steps selected from a RICC insertion assembly-obtaining step, a needle tract-establishing step, a blood-aspirating step, an access guidewire-advancing step, an introducer needle-withdrawing step, a RICC-advancing step, an access guidewire-withdrawing step, a maneuver guidewire-advancing step, another RICC-advancing step, and a maneuver guidewire-withdrawing step.

The RICC insertion assembly-obtaining step can include obtaining the RICC insertion assembly 100. As set forth above, the RICC insertion assembly 100 can include the RICC, the introducer needle 104, and the access guidewire 106 coupled together by the coupler 108. The coupler 108 can include the coupler housing 178 having the valve-module compartment 185 and the valve module 180 disposed in the valve-module compartment 185. The valve module 180 can include the gasket 198 encircling at least a portion of the valve-module compartment 185 of the coupler housing 178 along the length of the valve-module compartment 185. The gasket 198 in the valve-module compartment 185 of the coupler housing 178 can be compressed around the proximal portion of the introducer needle 104 and the distal portion of the access guidewire 106 in the ready-to-deploy state of the RICC insertion assembly 100, thereby creating the substantially air-tight space within the gasket 198 around the proximal portion of the introducer needle 104 and the distal portion of the access guidewire 106. Notably, the proximal end of the access guidewire 106 can also be coupled to the swivel arm 182 of the coupler 108 while the distal end of the access guidewire 106 is disposed in the introducer needle 104 by way of the valve module 180 of the coupler 108, thereby enforcing the loop in the access guidewire 106. And the RICC 102 can be disposed over the loop of the access guidewire 106 in the ready-to-deploy state of the RICC insertion assembly 100 keeping the RICC insertion assembly 100 in its relatively compact form as a result.

The needle tract-establishing step can include establishing a needle tract from an area of skin to the blood-vessel lumen with the introducer needle 104. Such a needle tract-establishing step can include a swivel arm-flipping step before puncturing the area of skin with the introducer needle 104. The needle tract-establishing step can also include a blood flashback-ensuring step while establishing the needle tract.

The swivel arm-flipping step can include flipping the swivel arm 182, and, thus, the loop between the two sides of the RICC insertion assembly 100. The swivel arm-flipping step can include flipping the loop between the sinistral side of the RICC insertion assembly 100 for a left-handed venipuncture and the dextral side of the RICC insertion assembly 100 for a right-handed venipuncture with the RICC insertion assembly 100. Indeed, the flipping of the loop from the sinistral side of the RICC insertion assembly 100 to the dextral side of the RICC insertion assembly 100 can accommodate the left-handed venipuncture with the RICC insertion assembly 100. Likewise, the flipping of the loop from the dextral side of the RICC insertion assembly 100 to the sinistral side of the RICC insertion assembly 100 can accommodate the right-handed venipuncture with the RICC insertion assembly 100.

The blood flashback-ensuring step can include ensuring blood flashback while establishing the needle tract. Ensuring the blood flashback can include witnessing blood flash back into the needle hub 144 of the introducer needle 104, the syringe tip 172 of the syringe 110 fluidly connected to the introducer needle 104, a barrel of the syringe 110, or a combination thereof. A slight vacuum can be drawn with the syringe 110 while establishing the needle tract such that the blood flashes back into at least the needle hub 144 of the introducer needle 104 upon the establishing of the needle tract. Ensuring the blood flashes back in accordance with the foregoing can confirm the needle tract extends into the blood-vessel lumen.

The blood-aspirating step can include aspirating blood with the syringe 110 fluidly connected to the introducer needle 104 for confirmation the needle tract extends into the blood-vessel lumen before performing the introducer needle-withdrawing step. The sheath 142 over the needle shaft 140 can seal the needle slot 148 thereunder except for the portion of the needle slot 148 under the sheath opening 162 of the sheath 142, which portion of the needle slot 148 can be sealed by the substantially air-tight space within the gasket 198 for the aspirating of the blood with the syringe 110.

The access guidewire-advancing step can include advancing the distal end of the access guidewire 106 from its initial location in the needle shaft 140 just proximal of the needle tip 146 of the needle shaft 140 into the blood-vessel lumen, thereby securing blood-vessel access for the RICC 102 in the RICC-advancing step. To accomplish the foregoing, the access guidewire 106 can be initially advanced into the access-guidewire channel 206 through the proximal-end portion of the gasket 198 using, for example, a thumb and index finger to pinch the access guidewire 106 and push it into the access-guidewire channel 206 with an acceptable level of force. As set forth above, the access-guidewire channel 206 can form the acute angle with the proximal needle through-hole 202, thereby directing the distal portion of the access guidewire 106 into the opening in the side of the introducer needle 104, specifically the sheath opening 162 of the sheath 142 and the needle slot 148 of the needle shaft 140.

The introducer needle-withdrawing step can include withdrawing the introducer needle 104 from the coupler 108, thereby leaving the access guidewire 106 in place in the blood-vessel lumen. Before the introducer needle 104 is completely withdrawn from the coupler 108, the introducer needle 104 is withdrawn from the gasket 198. Specifically, the introducer needle 104 can be withdrawn from the proximal needle through-hole 202 through the proximal-end portion of the gasket 198 and the distal needle through-hole 204 through the distal-end portion of the gasket 198. As the introducer needle 104 is withdrawn from the proximal and distal needle through-holes 202 and 204 of the gasket 198, the sheath 142 can be simultaneously cut off the needle shaft 140 with the access guidewire 106, itself, or the blade 192 extending into the valve module 180 through the gasket 198. The cutting of the sheath 142 off the needle shaft 140 allows the access guidewire 106 to escape from the needle shaft 140 by way of the needle slot 148 thereof. Again, the unitary-piece embodiment of the gasket 198 can include the slit 200 in the top portion of the gasket 198, thereby further allowing the access guidewire 106 to escape from the top portion of the gasket 198 as the introducer needle 104 is withdrawn from the coupler 108. Notably, the slit 200 in the top portion of the unitary-piece embodiment of the gasket 198 can continue through the bottom portion of the gasket 198 formed of the two complementary, substantially mirror-imaged pieces mated together. Indeed, the plane of symmetry set forth above for the two-piece embodiment of the gasket 198 can be coincident with and continue the slit 200 in the top portion of the unitary-piece embodiment of the gasket 198 through the bottom portion of the two-piece embodiment of the gasket 198, thereby further allowing the access guidewire 106 to escape from the bottom portion of the gasket 198 as the introducer needle 104 is withdrawn from the coupler 108. Lastly, the coupler housing 178 can include the coupler-housing slot 186 configured to further allow the access guidewire 106 to escape from the coupler housing 178 when the introducer needle 104 is withdrawn from the coupler 108.

The RICC-advancing step can include advancing the catheter tube 112 of the RICC 102 over the access guidewire 106 and into the blood-vessel lumen, thereby inserting the RICC 102 into the blood-vessel lumen.

The access guidewire-withdrawing step can include withdrawing the access guidewire 106, thereby leaving the catheter tube 112 in place in the blood-vessel lumen.

The maneuver guidewire-advancing step can include advancing a maneuver guidewire into the blood-vessel lumen by way of the primary lumen 128 of the RICC 102 and to a lower ⅓ of an SVC of a heart of the patient.

The other RICC-advancing step can include advancing the distal portion of the catheter tube 112 farther into the blood-vessel lumen over the maneuver guidewire to the lower ⅓ of the SVC of the heart of the patient.

The maneuver guidewire-withdrawing step can include withdrawing the maneuver guidewire, thereby leaving the catheter tube 112 in place in the lower ⅓ of the SVC.

Methods of the introducer assembly 208 can include a method for establishing access to a blood-vessel lumen of a patient. Such a method can include one or more steps selected from an introducer assembly-obtaining step, a needle tract-establishing step, a blood-aspirating step, an access guidewire-advancing step, an introducer needle-withdrawing step, a dilating step, a catheter-threading step, and a catheter-advancing step.

The introducer assembly-obtaining step can include obtaining the introducer assembly 208. As set forth above, the introducer assembly 208 can include the introducer needle 104, the access guidewire 106, and the coupler 108 coupling together the introducer needle 104 and the access guidewire 106. Optionally, the introducer assembly 208 can further include the syringe 110 fluidly coupled to the introducer needle 104. The coupler 108 can include the coupler housing 178 having the valve-module compartment 185 and the valve module 180 disposed in the valve-module compartment 185. The valve module 180 can include the gasket 198 encircling at least a portion of the valve-module compartment 185 of the coupler housing 178 along the length of the valve-module compartment 185. The gasket 198 in the valve-module compartment 185 of the coupler housing 178 can be compressed around the proximal portion of the introducer needle 104 and the distal portion of the access guidewire 106 in the ready-to-deploy state of the introducer assembly 208, thereby creating the substantially air-tight space within the gasket 198 around the proximal portion of the introducer needle 104 and the distal portion of the access guidewire 106.

The needle tract-establishing step can include establishing a needle tract from an area of skin to the blood-vessel lumen with the introducer needle 104. Like that set forth above, the needle tract-establishing step can also include a blood flashback-ensuring step while establishing the needle tract. Again, ensuring the blood flashes back into the needle hub 144 of the introducer needle 104, the syringe tip 172 of the syringe 110 fluidly connected to the introducer needle 104, the barrel of the syringe 110, or a combination thereof can confirm the needle tract extends into the blood-vessel lumen.

The blood-aspirating step can include aspirating blood with the syringe 110 fluidly connected to the introducer needle 104 for confirmation the needle tract extends into the blood-vessel lumen before performing the introducer needle-withdrawing step. The sheath 142 over the needle shaft 140 can seal the needle slot 148 thereunder except for the portion of the needle slot 148 under the sheath opening 162 of the sheath 142, which portion of the needle slot 148 can be sealed by the substantially air-tight space within the gasket 198 for the aspirating of the blood with the syringe 110.

The access guidewire-advancing step can include advancing the distal end of the access guidewire 106 from its initial location in the needle shaft 140 just proximal of the needle tip 146 of the needle shaft 140 into the blood-vessel lumen, thereby securing blood-vessel access for the dilator in the dilating step, when performed, and the CVC in the catheter-advancing step. Like that set forth above, the access guidewire 106 can be initially advanced into the access-guidewire channel 206 through the proximal-end portion of the gasket 198 using, for example, a thumb and index finger to pinch the access guidewire 106 and push it into the access-guidewire channel 206 with an acceptable level of force. Again, the access-guidewire channel 206 can form the acute angle with the proximal needle through-hole 202, thereby directing the distal portion of the access guidewire 106 into the opening in the side of the introducer needle 104, specifically the sheath opening 162 of the sheath 142 and the needle slot 148 of the needle shaft 140.

The introducer needle-withdrawing step can include withdrawing the introducer needle 104 from the coupler 108, thereby leaving the access guidewire 106 in place in the blood-vessel lumen. Like that set forth above, the introducer needle 104 is withdrawn from the gasket 198 before the introducer needle 104 is completely withdrawn from the coupler 108. Specifically, the introducer needle 104 can be withdrawn from the proximal needle through-hole 202 through the proximal-end portion of the gasket 198 and the distal needle through-hole 204 through the distal-end portion of the gasket 198. As the introducer needle 104 is withdrawn from the proximal and distal needle through-holes 202 and 204 of the gasket 198, the sheath 142 can be simultaneously cut off the needle shaft 140 with the access guidewire 106, itself, or the blade 192 extending into the valve module 180 through the gasket 198. The cutting of the sheath 142 off the needle shaft 140 allows the access guidewire 106 to escape from the needle shaft 140 by way of the needle slot 148 thereof. Again, the unitary-piece embodiment of the gasket 198 can include the slit 200 in the top portion of the gasket 198, thereby further allowing the access guidewire 106 to escape from the top portion of the gasket 198 as the introducer needle 104 is withdrawn from the coupler 108. Notably, the slit 200 in the top portion of the unitary-piece embodiment of the gasket 198 can continue through the bottom portion of the gasket 198 formed of the two complementary, substantially mirror-imaged pieces mated together. Indeed, the plane of symmetry set forth above for the two-piece embodiment of the gasket 198 can be coincident with and continue the slit 200 in the top portion of the unitary-piece embodiment of the gasket 198 through the bottom portion of the two-piece embodiment of the gasket 198, thereby further allowing the access guidewire 106 to escape from the bottom portion of the gasket 198 as the introducer needle 104 is withdrawn from the coupler 108. Lastly, the coupler housing 178 can include the coupler-housing slot 186 configured to further allow the access guidewire 106 to escape from the coupler housing 178 when the introducer needle 104 is withdrawn from the coupler 108.

The dilating step can include dilating tissue around the needle tract with a dilator before threading the catheter tube of the CVC over the proximal portion of the access guidewire 106 in the catheter-threading step. Like the catheter-threading step and the catheter-advancing step set forth below, the dilating step can include a dilator-threading step of threading the dilator over the proximal portion of the access guidewire 106 and a dilator-advancing step of advancing the dilator over the access guidewire 106 and into the blood-vessel lumen.

The catheter-threading step can include threading a catheter tube of a CVC over the proximal portion of the access guidewire 106. While the CVC can be the RICC 102 set forth herein, it should be understood that any CVC can be used in this method. Further, when the RICC 102 is used as the CVC, the dilating step need not be performed as the RICC 102 is configured to obviate the dilating step.

The catheter-advancing step can include advancing the catheter tube of the CVC over the access guidewire 106 and into the blood-vessel lumen.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A rapidly insertable central-catheter ("RICC") insertion assembly, comprising:

a RICC;

an introducer needle including:

a needle shaft including a longitudinal needle slot extending from a proximal portion of the needle shaft through a distal needle tip; and a sheath over the needle shaft sealing the needle slot thereunder except for a portion of the needle slot under a sheath opening in a proximal portion of the sheath;

a coupler coupling the RICC and the introducer needle together, the coupler including:

a coupler housing including a valve-module compartment; and a valve module disposed in the valve-module compartment of the coupler housing, the valve module including:

an elastomeric gasket encircling at least a portion of the valve-module compartment of the coupler housing along a length of the valve-module compartment, the gasket in the valve-module compartment compressed around a proximal portion of the introducer needle in a ready-to-deploy state of the RICC insertion assembly to create a substantially air-tight space within the gasket around the proximal portion of the introducer needle; and an access guidewire including:

a distal portion passing into the introducer needle through both the sheath opening of the sheath and the needle slot of the needle shaft, the gasket in the valve-module compartment also compressed around the distal portion of the access guidewire in the ready-to-deploy state of the RICC insertion assembly to create the substantially air-tight space within the gasket around the distal portion of the access guidewire; and a distal end disposed in the introducer needle just proximal of a needle tip in a distal end of the introducer needle.

2. The RICC insertion assembly of claim 1, wherein the gasket is formed of a unitary piece.

3. The RICC insertion assembly of claim 2, wherein the gasket includes a proximal needle through-hole through a proximal-end portion of the gasket and a distal needle through-hole aligned with the proximal needle through-hole through a distal-end portion of the gasket, the proximal portion of the introducer needle passing through both the proximal needle through-hole and the distal needle through-hole in the ready-to-deploy state of the RICC insertion assembly.

4. The RICC insertion assembly of claim 3, wherein the gasket includes an access-guidewire channel through the proximal-end portion of the gasket, the access-guidewire channel forming an acute angle with the proximal needle through-hole, thereby directing the distal portion of the access guidewire into the proximal portion of the introducer needle through both the sheath opening of the sheath and the needle slot of the needle shaft.

5. The RICC insertion assembly of claim 4, wherein the access-guidewire channel is coincident with a terminal portion of a longitudinal slit through a top portion of the gasket.

6. The RICC insertion assembly of claim 5, wherein the access-guidewire channel has an inner diameter commensurate with an outer diameter of the access guidewire.

7. The RICC insertion assembly of claim 5, wherein the distal needle through-hole is coincident with a second terminal portion of the longitudinal slit through the top portion of the gasket.

8. The RICC insertion assembly of claim 7, wherein the distal needle through-hole has an inner diameter commensurate with an outer diameter of the introducer needle.

9. The RICC insertion assembly of claim 5, wherein the longitudinal slit is configured to separate and allow the access guidewire to escape from the top portion of the gasket when compression on the gasket is relieved and the introducer needle is withdrawn from the coupler.

10. The RICC insertion assembly of claim 1, wherein the gasket is formed of two complementary pieces of the gasket mated together.

11. The RICC insertion assembly of claim 10, wherein the gasket is substantially symmetric along a longitudinal plane of symmetry through a majority of the gasket, the two complementary pieces of the gasket substantially being mirror images of each other.

12. The RICC insertion assembly of claim 10, wherein the gasket is asymmetric, the two complementary pieces of the gasket not related to each other by any symmetry operation.

13. The RICC insertion assembly of claim 10, wherein the gasket includes a proximal needle through-hole through a proximal-end portion of the gasket and a distal needle through-hole aligned with the proximal needle through-hole through a distal-end portion of the gasket, each through-hole of the proximal needle through-hole and the distal needle through-hole formed between the two complementary pieces of the gasket mated together, and the proximal portion of the introducer needle passing through both the proximal needle through-hole and the distal needle through-hole in the ready-to-deploy state of the RICC insertion assembly.

14. The RICC insertion assembly of claim 13, wherein the gasket includes an access-guidewire channel through the proximal-end portion of the gasket, the access-guidewire channel formed between the two complementary pieces of the gasket mated together, and the access-guidewire channel forming an acute angle with the proximal needle through-hole, thereby directing the distal portion of the access guidewire into the introducer needle through both the sheath opening of the sheath and the needle slot of the needle shaft.

15. The RICC insertion assembly of claim 10, wherein the two complementary pieces of the gasket are configured to separate and allow the access guidewire to escape from the gasket when compression on the gasket is relieved and the introducer needle is withdrawn from the coupler.

16. The RICC insertion assembly of claim 1, wherein the gasket approximates a rectangle in a side-on view of the gasket.

17. The RICC insertion assembly of claim 1, wherein the gasket approximates a right trapezoid in a side-on view of the gasket.

18. The RICC insertion assembly of claim 1, the coupler further including a blade coupled to the coupler housing, the blade extending into the valve module through the gasket such that a distal facing blade edge is disposed in the needle slot of the needle shaft under a distal end of the sheath opening of the sheath for cutting the sheath off the needle shaft as the introducer needle is withdrawn from the coupler, thereby allowing the access guidewire to escape from the needle shaft through the needle slot.

19. The RICC insertion assembly of claim 1, wherein the coupler housing includes a longitudinal coupler-housing slot configured to allow the access guidewire to escape from the coupler housing when the introducer needle is withdrawn from the coupler.

20. The RICC insertion assembly of claim 1, the coupler further including a compression clip over complementary mated pieces of the coupler housing, the compression clip configured to compress the gasket in the valve-module compartment.

21. The RICC insertion assembly of claim 1, the coupler further including one or more lubricant wells including a lubricant, one or more lubricant receptors configured to receive or redistribute the lubricant, or a combination thereof.

22. The RICC insertion assembly of claim 1, further comprising:

a syringe fluidly coupled to the introducer needle in the ready-to-deploy state of the RICC insertion assembly.

* * * * *